(12) United States Patent
Zhang et al.

(10) Patent No.: US 8,727,972 B2
(45) Date of Patent: May 20, 2014

(54) LOW PROFILE BONE SCREW EXTENDER AND ITS APPLICATION IN MINIMUM INVASIVE SPINAL SURGERIES

(75) Inventors: Jeffrey Zhang, Collierville, TN (US); Randall N. Allard, Issaquah, WA (US); Frank J. Schwab, New York, NY (US); Lawrence G. Lenke, St. Louis, MO (US); Carlos E. Gil, Collierville, TN (US); Greg C. Marik, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 746 days.

(21) Appl. No.: 12/364,621

(22) Filed: Feb. 3, 2009

(65) Prior Publication Data
US 2010/0198268 A1 Aug. 5, 2010

(51) Int. Cl.
*A61B 1/32* (2006.01)

(52) U.S. Cl.
USPC .............................. 600/206; 600/210; 606/279

(58) Field of Classification Search
USPC ........... 411/57.1, 59; 606/327, 328, 313, 279, 606/206; 600/210, 206
See application file for complete search history.

(56) References Cited

U.S. PATENT DOCUMENTS

| | | |
|---|---|---|
| 7,179,261 B2 | 2/2007 | Sicvol et al. |
| 7,303,562 B2 | 12/2007 | Cavagna et al. |
| 2001/0012937 A1 | 8/2001 | Schaffler-Wachter |
| 2002/0007184 A1 | 1/2002 | Ogilvie et al. |
| 2003/0004511 A1* | 1/2003 | Ferree .............................. 606/61 |
| 2004/0034351 A1 | 2/2004 | Sherman et al. |
| 2004/0215191 A1 | 10/2004 | Kitchen |
| 2006/0276803 A1 | 12/2006 | Salerni |
| 2007/0106123 A1* | 5/2007 | Gorek et al. ................... 600/210 |
| 2007/0162007 A1 | 7/2007 | Shoham |
| 2007/0270842 A1 | 11/2007 | Bankoski et al. |
| 2008/0015584 A1* | 1/2008 | Richelsoph ..................... 606/61 |
| 2008/0077134 A1 | 3/2008 | Dziedzic et al. |

OTHER PUBLICATIONS

International Searching Authority, International Search Report and Written Opinion for USPCT/US2010/022705 mailed on Aug. 23, 2010.

* cited by examiner

*Primary Examiner* — Bruce E Snow
(74) *Attorney, Agent, or Firm* — Sorell Lenna & Schmidt LLP

(57) ABSTRACT

A tissue extender includes a ring defining a proximal end opening to engage a head of a subcutaneous screw, a first extender portion coupled to the ring at a proximal end of the first extender portion, and a second extender portion coupled to the ring at a proximal end of the second extender portion. The first extender portion includes a first coupling portion disposed at a distal end of the first extender portion, and the second extender portion includes a second coupling portion at a distal end of the second extender portion. The first and second extender portions define two side openings disposed on opposite sides of the tissue extender. The distal ends of the first and second extender portions together define a distal end opening. The first coupling portion engages the second coupling portion when the tissue extender is in an extended state. The distal end opening is larger in the extended state than in an unextended state.

26 Claims, 23 Drawing Sheets

LOW PROFILE BONE SCREW EXTENDER AND ITS APPLICATION IN MINIMUM INVASIVE SPINAL SURGERIES

FIELD OF THE DISCLOSURE

The present disclosure relates generally to orthopedics and orthopedic surgery. More specifically, the present disclosure relates to methods and devices for insertion of tethers through subcutaneous screw heads.

BACKGROUND

In human anatomy, the spine is a generally flexible column that can take tensile and compressive loads. The spine also allows bending motion and provides a place of attachment for tendons, muscles and ligaments. Generally, the spine is divided into four sections: the cervical spine, the thoracic or dorsal spine, the lumbar spine, and the pelvic spine. The pelvic spine generally includes the sacrum and the coccyx. The sections of the spine are made up of individual bones called vertebrae. Also, the vertebrae are separated by intervertebral discs, which are situated between adjacent vertebrae.

The intervertebral discs function as shock absorbers and as joints. Further, the intervertebral discs can absorb the compressive and tensile loads to which the spinal column may be subjected. At the same time, the intervertebral discs can allow adjacent vertebral bodies to move relative to each other a limited amount, particularly during bending or flexure of the spine. Thus, the intervertebral discs are under constant muscular and gravitational pressure and generally, the intervertebral discs are the first parts of the lumbar spine to show signs of deterioration or degeneration.

Facet joint degeneration is also common because the facet joints are in almost constant motion with the spine. In fact, facet joint degeneration and disc degeneration frequently occur together. Generally, although one may be the primary problem while the other is a secondary problem resulting from the altered mechanics of the spine, by the time surgical options are considered, both facet joint degeneration and disc degeneration typically have occurred. For example, the altered mechanics of the facet joints and the intervertebral disc may cause spinal stenosis, degenerative spondylolisthesis, and degenerative scoliosis.

In addition to degeneration, the spine may be injured through traumatic events, such as automobile accidents, falls, or over exertion. Such spinal injuries may lead to surgery to repair broken vertebra or to fortify the spine.

However, such surgeries tend to utilize large incisions and extensive tissue retraction. In many typical surgeries, muscle and ligament tissues are retracted or are surgically detached during the surgery and reattached afterward. As a result, such surgeries lead to long recovery time, patient discomfort, an increased risk of infection, and high expense.

As such, an improved apparatus and method for performing spinal surgeries would be desirable.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

In a particular embodiment, a surgical assembly includes a subcutaneous screw, a tissue extender, and a setscrew. The tissue extender may include a ring and two extender portions that define a distal end opening and two side openings. The side openings may be larger than a slot in a head of the subcutaneous screw. The ring of the tissue extender may engage the head of the subcutaneous screw. In particular, a plurality of such surgical assemblies may be useful in spinal surgeries, particularly those that secure or tether adjacent vertebrae together.

In an additional embodiment, a surgical method includes implanting a surgical assembly that includes a subcutaneous screw and a tissue extender. The tissue extender may be coupled to a head of the subcutaneous screw prior to implanting the screw. As the screw is driven into hard tissue within the body, the tissue extender may retract soft tissue. In addition, the tissue extender may be expanded to further retract the soft tissue. In an example, a tether is threaded percutaneously and through the openings of the tissue extender. Further, the tether may be lock into the head of the subcutaneous screw using a setscrew. The tissue extender may be removed and the surgical incision closed.

Description of Relevant Anatomy

Figure 1:
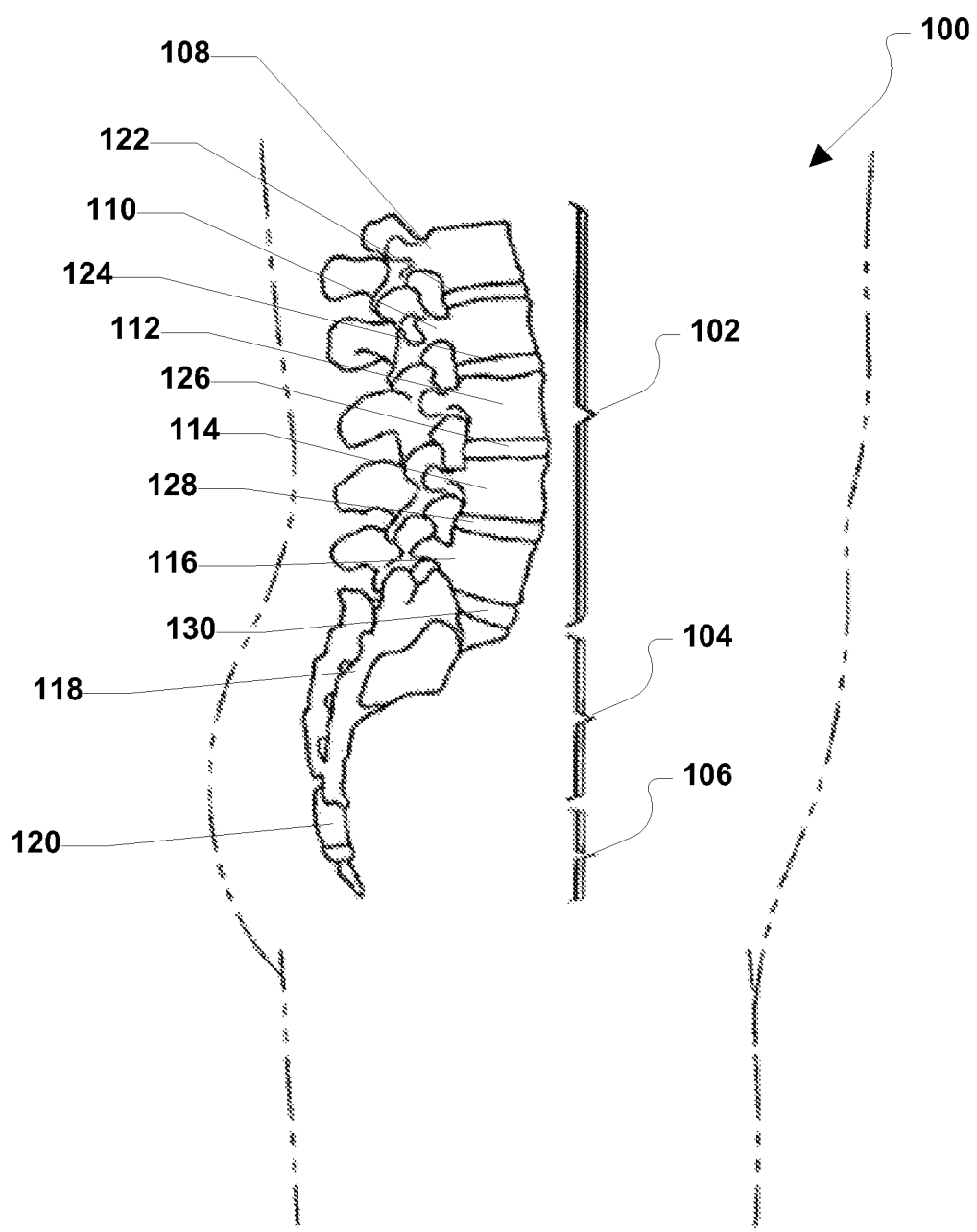
FIG. 1 includes a lateral view illustration of a portion of a vertebral column.

Referring initially to FIG. 1, a portion of a vertebral column, designated 100, is illustrated. As depicted, the vertebral column 100 includes a lumbar region 102, a sacral region 104, and a coccygeal region 106. The vertebral column 100 also includes a cervical region and a thoracic region. For clarity and ease of discussion, the cervical region and the thoracic region are not illustrated.

As illustrated in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, misalignment of two or more vertebra (108, 110, 112, 114, or 116) or damage to the facet joints may be treated in accordance with one or more of the embodiments described herein.

Figure 2:
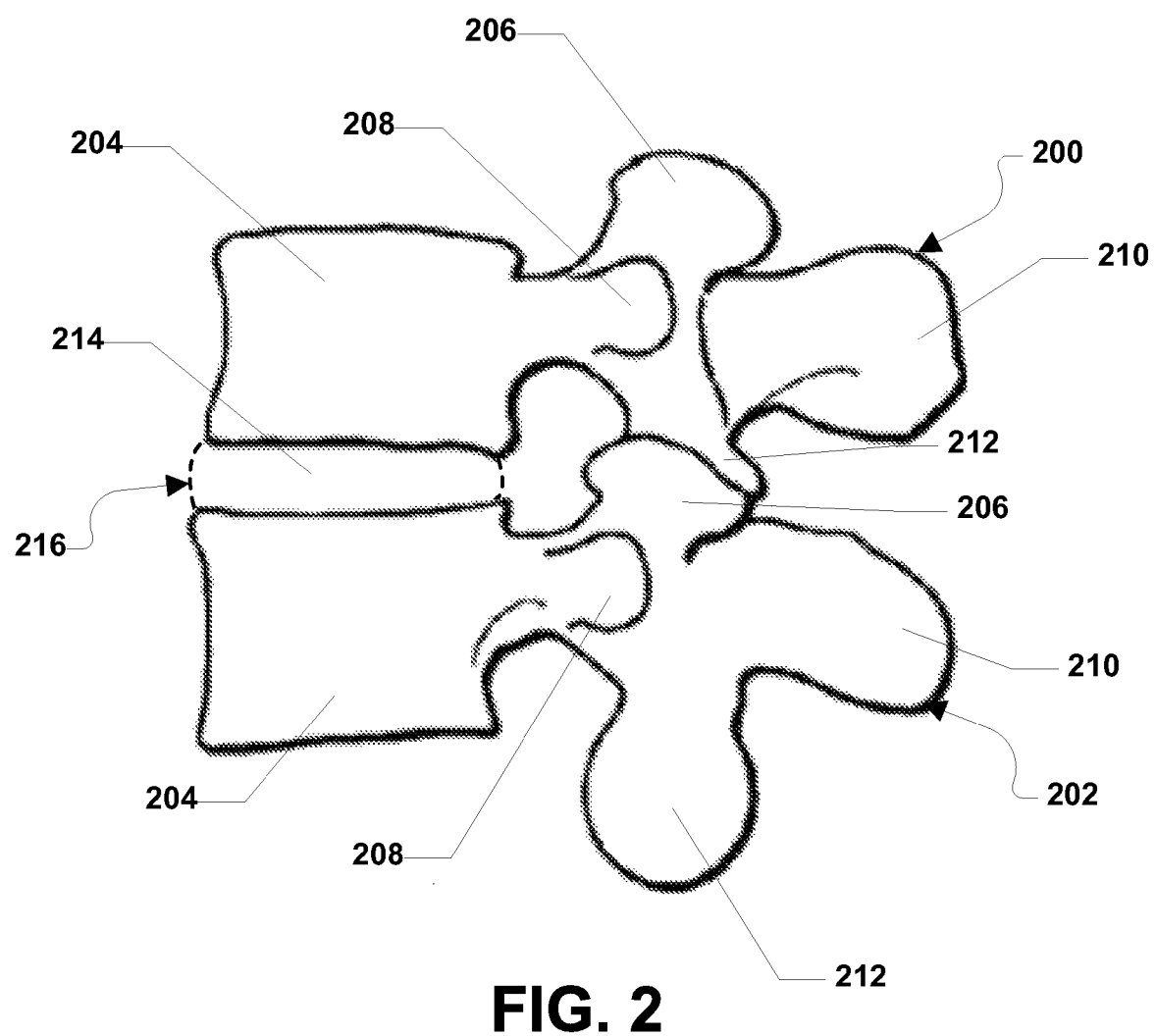
FIG. 2 includes a lateral view illustration of a pair of adjacent vertebrae.

FIG. 2 depicts a detailed lateral view of two adjacent vertebrae, e.g., two of the lumbar vertebra 108, 110, 112, 114, 116 illustrated in FIG. 1. FIG. 2 illustrates a superior vertebra 200 and an inferior vertebra 202. As illustrated, each vertebra 200, 202 includes a vertebral body 204, a superior articular process 206, a transverse process 208, a spinous process 210 and an inferior articular process 212. FIG. 2 further depicts an intervertebral disc 214 between the superior vertebra 200 and the inferior vertebra 202.

Figure 3:
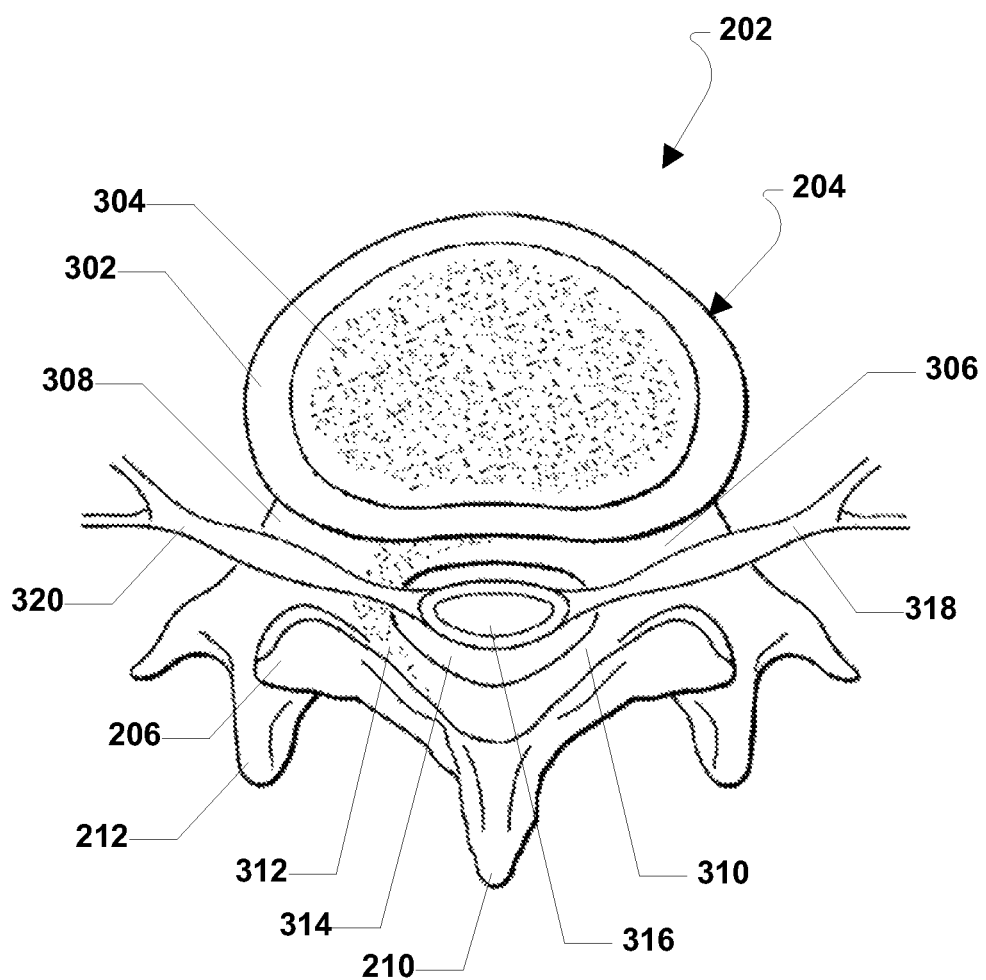
FIG. 3 includes a top plan view illustration of a vertebra.

Referring to FIG. 3, a vertebra, e.g., the inferior vertebra 202 (FIG. 2), is illustrated. As illustrated, the vertebral body 204 of the inferior vertebra 202 includes a cortical rim 302 composed of cortical bone. Also, the vertebral body 204 includes cancellous bone 304 within the cortical rim 302. The cortical rim 302 is often referred to as the apophyseal rim or apophyseal ring. Further, the cancellous bone 304 is softer than the cortical bone of the cortical rim 302.

As illustrated in FIG. 3, the inferior vertebra 202 further includes a first pedicle 306, a second pedicle 308, a first lamina 310, and a second lamina 312. Further, a spinal canal 314 is established within the inferior vertebra 202. A spinal cord 316 passes through the spinal canal 314. Moreover, a first nerve root 318 and a second nerve root 320 extend from the spinal cord 316.

The vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2 and FIG. 3. The first and second cervical vertebrae are structurally different than the rest of the vertebrae in order to support a skull.

Description of a Percutaneous Surgical Assembly

In a particular embodiment, a percutaneous surgical assembly includes a subcutaneous screw coupled to a percutaneous tissue extender. When in use, the subcutaneous screw may engage a hard tissue structure, such as an osteal structure, and the tissue extender may extend from a head of the subcutaneous screw through soft tissue including the skin.

Figure 4:
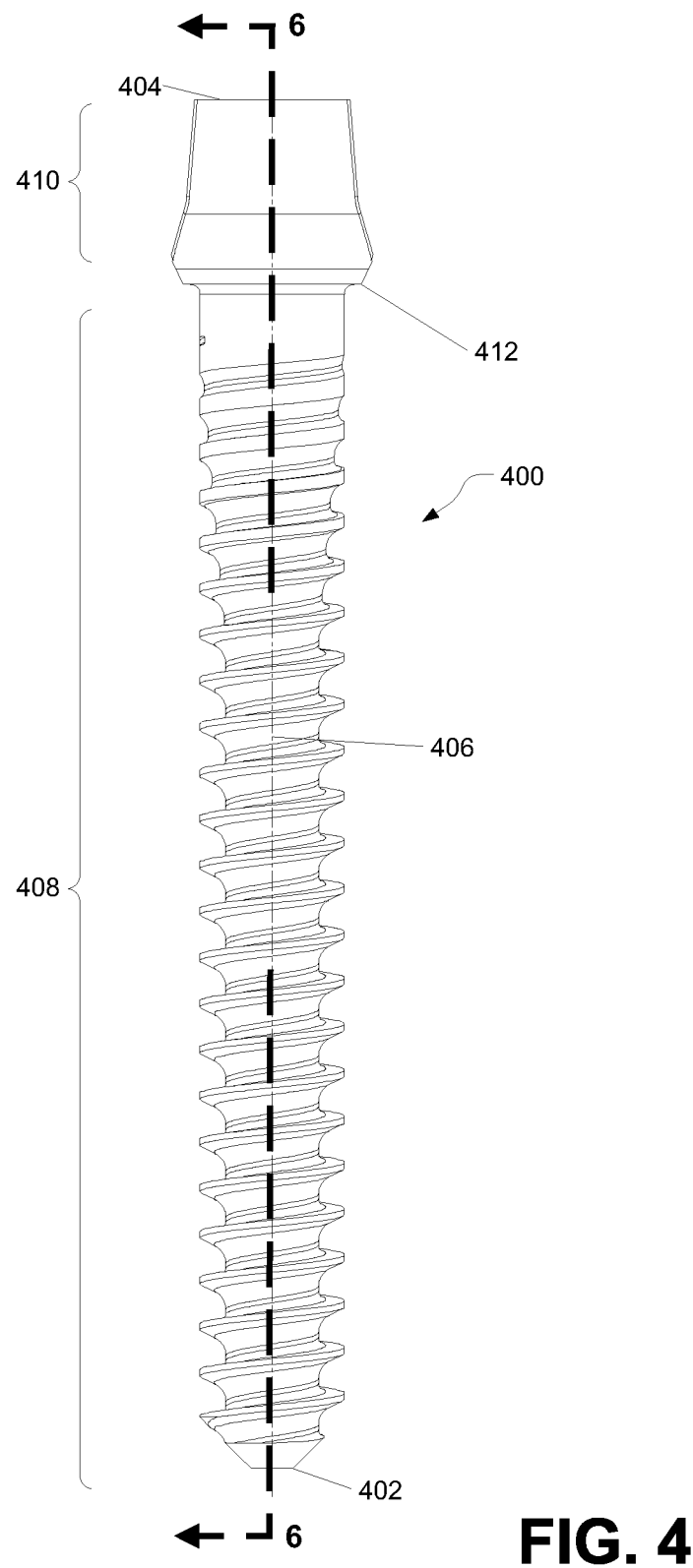
FIG. 4, FIG. 5 and FIG. 6 include an illustration of an exemplary subcutaneous screw.
Figure 5:
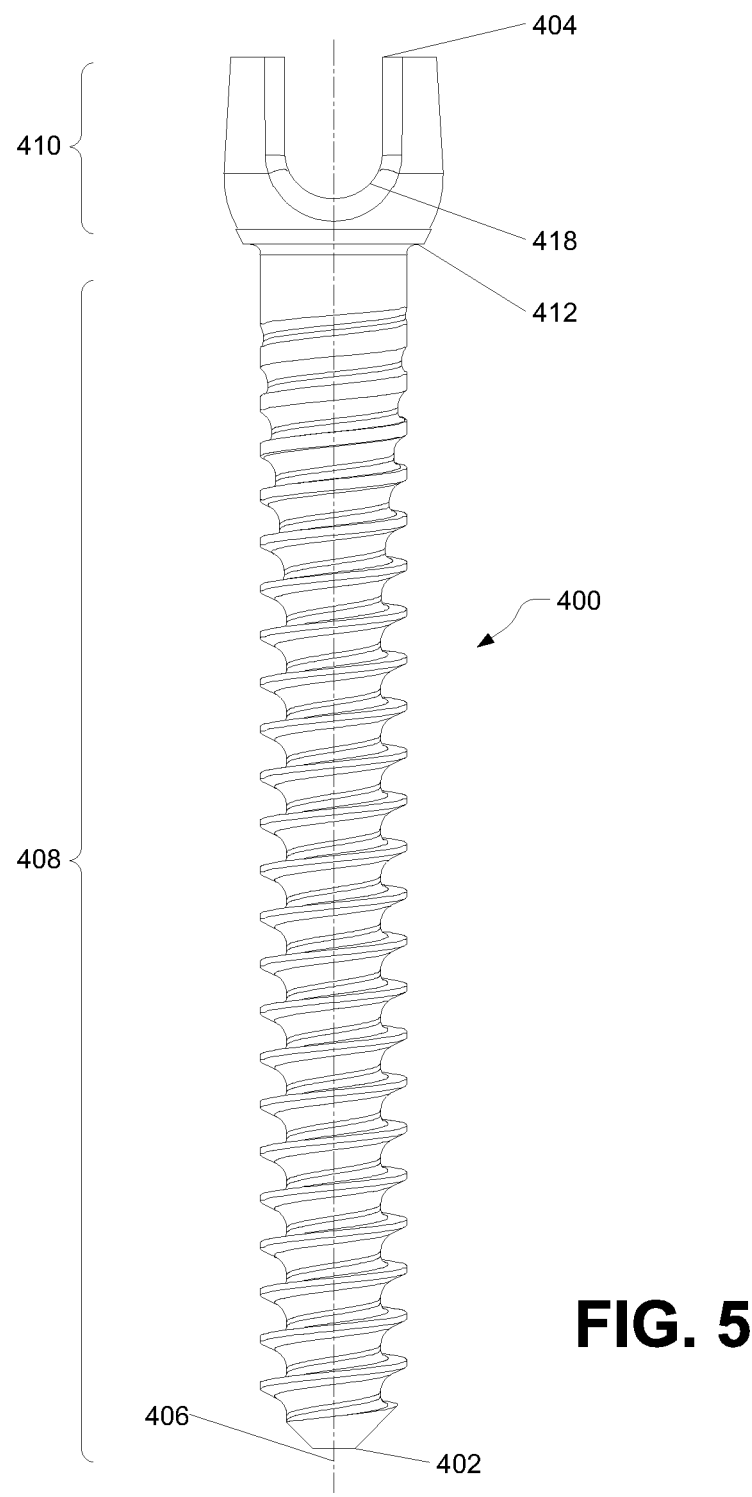
Figure 6:
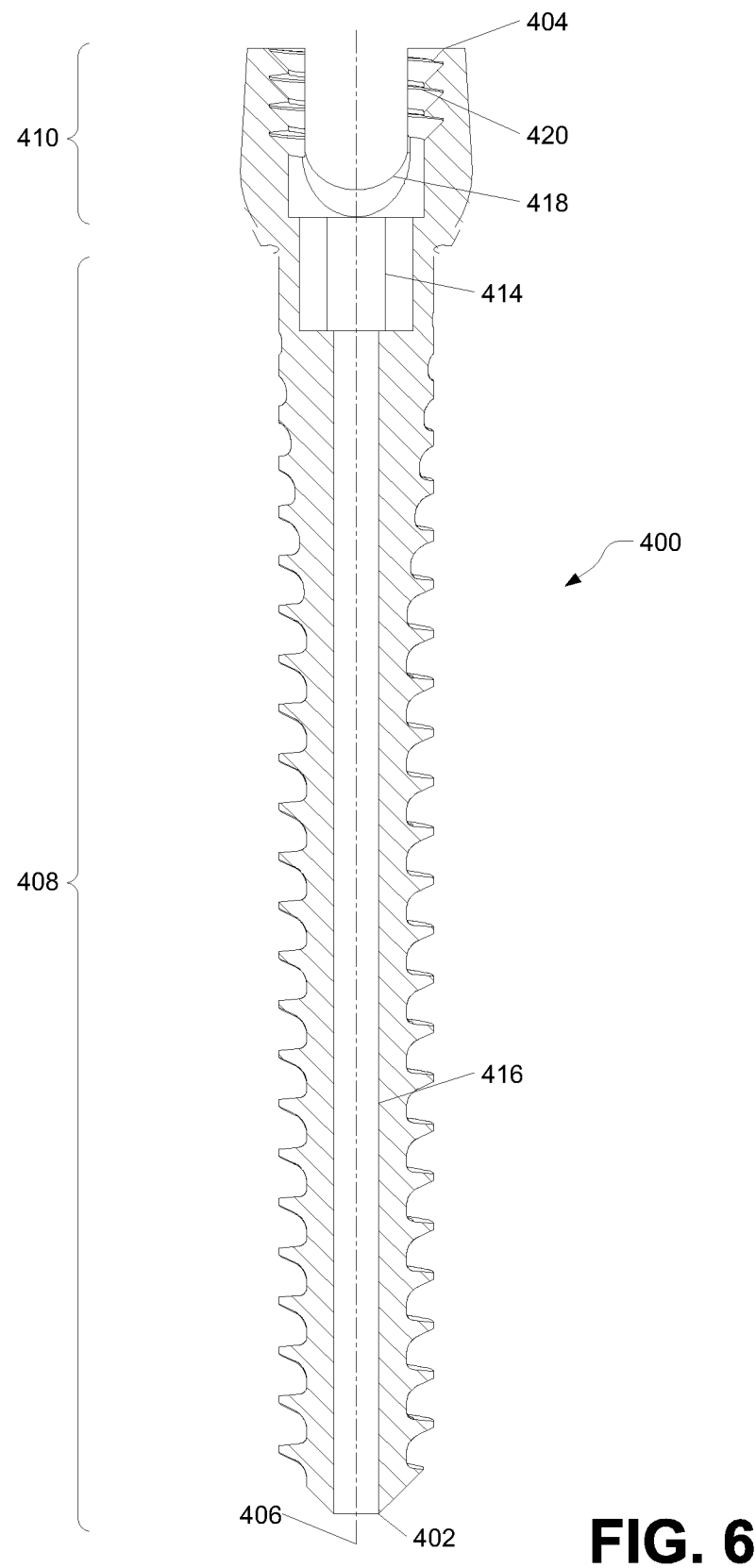

FIG. 4, FIG. 5, and FIG. 6 illustrate an embodiment of a subcutaneous screw 400. In an exemplary embodiment, the subcutaneous screw is a pedicle screw. As illustrated in FIG. 4 and FIG. 5, the subcutaneous screw may include a proximal end 402, a distal end 404, and a major axis 406. The subcutaneous screw 400 may have a threaded shaft 408 and a head 410 attached to the threaded shaft 408. As illustrated, the head 410 is fixedly attached to the threaded shaft 408. Alternatively, the head 410 may be rotationally fixed to the threaded shaft 408, such as rotatably around one or more axis.

In addition, the head 410 may include a lip 412, for example, located proximally to where the head 410 is joined to the threaded shaft 408. In an example, the lip 412 substantially prevents the subcutaneous screw 400 from being inserted too far into a bone. Additionally, the lip 412 may be configured to receive a tissue extender.

As illustrated in FIG. 6, a tool engagement depression 414 may be formed within the subcutaneous screw 400. The tool engagement depression 414 may be formed partially in the threaded shaft 408 and the head 410 of the subcutaneous screw 400. The tool engagement depression 414 may be shaped to receive a tool for rotationally driving the subcutaneous screw 400 into an osteal structure, such as a pedicle of a vertebral bone. In an example, the tool engagement depression 414 has a hexagonal cross section to receive a hex bit.

Further, the threaded shaft 408 may include a central bore 416. In an embodiment, a probe or guidewire extends through the central bore 416 of the subcutaneous screw 400. The guidewire may be used to guide the placement of the subcutaneous screw 400 and may be used to influence both position and orientation of the subcutaneous screw 400. In particular, the guidewire may be used to guide the subcutaneous screw 400 to a position on a bone that has been tapped in preparation for insertion of the subcutaneous screw 400 and to assist in orienting the subcutaneous screw 400.

The head 410 of the subcutaneous screw 400 may include a slot 418 extending across the head 410 and an inner threaded lumen 420 extending coaxially with the central bore 416. The slot 418 and the inner threaded lumen may intersect, as illustrated in FIG. 6. The slot 418 may be configured to receive an elongate fixing element, such as a rod, a wire, or a tether. The inner threaded portion 420 may be configured to receive a setscrew. In an embodiment, the setscrew secures the elongate fixing element within the head 410 of the subcutaneous screw 400.

Figure 7:
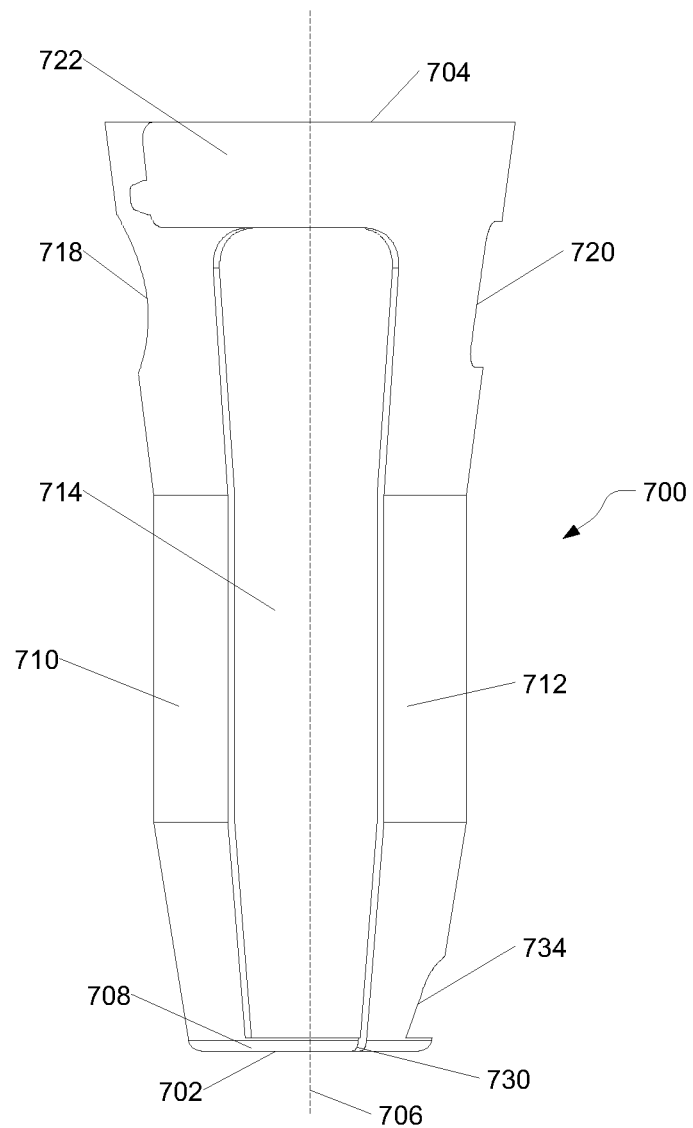
FIG. 7, FIG. 8, FIG. 9, FIG. 10, FIG. 11, and FIG. 12 include illustrations of an exemplary tissue extender.

A tissue extender may be coupled to the head 410 of the subcutaneous screw. Referring to FIG. 7, FIG. 8, FIG. 9, FIG. 10, FIG. 11, and FIG. 12, an embodiment of a tissue extender 700 is illustrated. As illustrated in FIG. 7, the tissue extender 700 may have a proximal end 702 and a distal end 704 disposed along a major axis 706. At the proximal end 702, the tissue extender 700 may have a ring 708. The ring 708 may engage a head of a subcutaneous screw, such as the head 410 of the subcutaneous screw 400. Extender portions 710 and 712 may be attached to the ring 708 and may extend axially from the proximal end 702 to the distal end 704.

Figure 8:
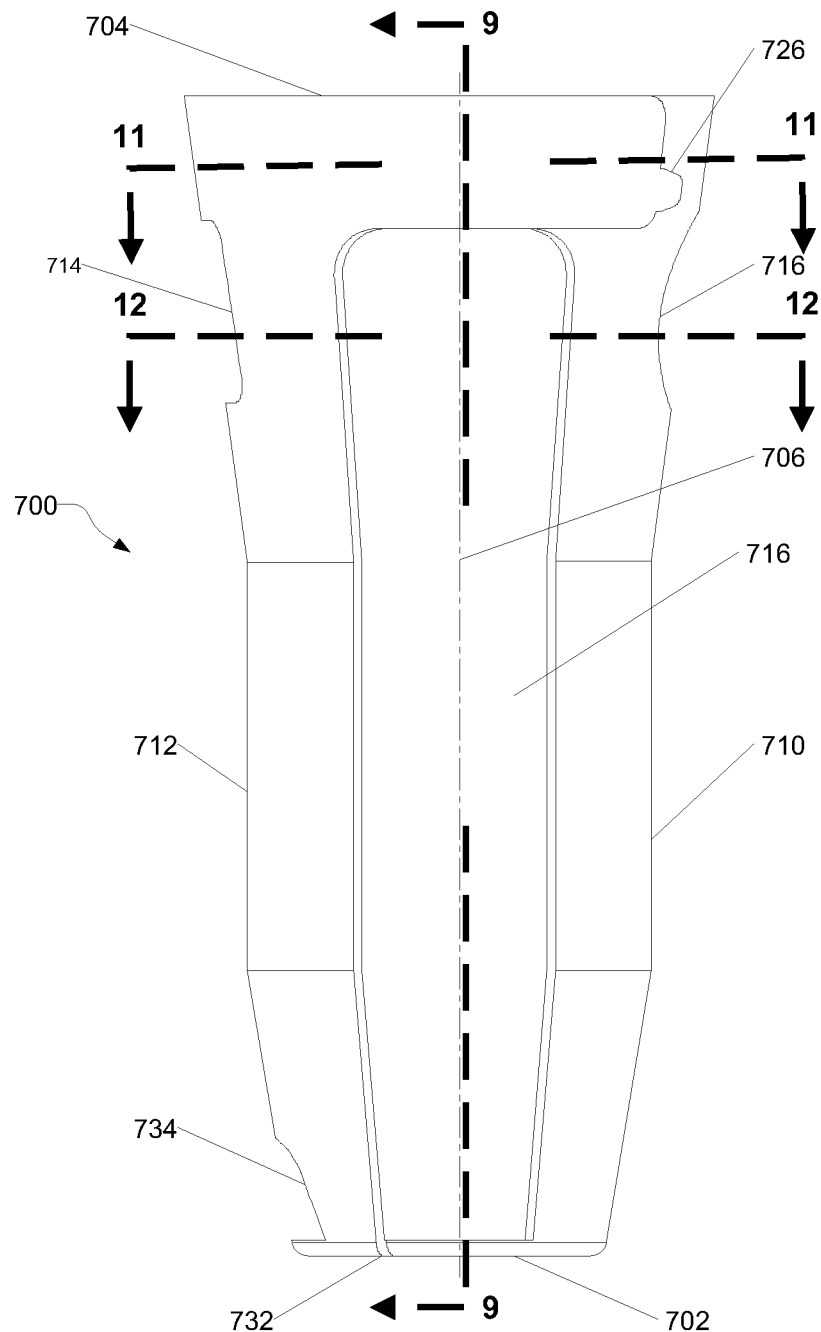
Figure 9:
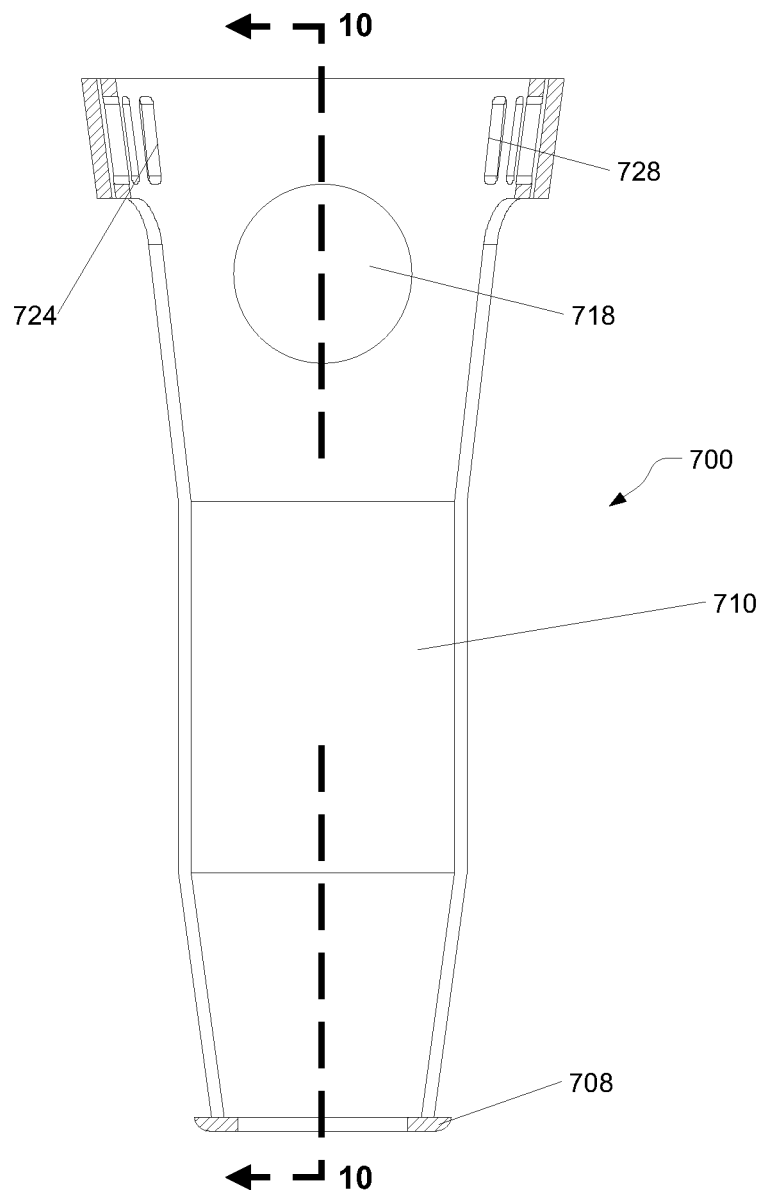
Figure 10:
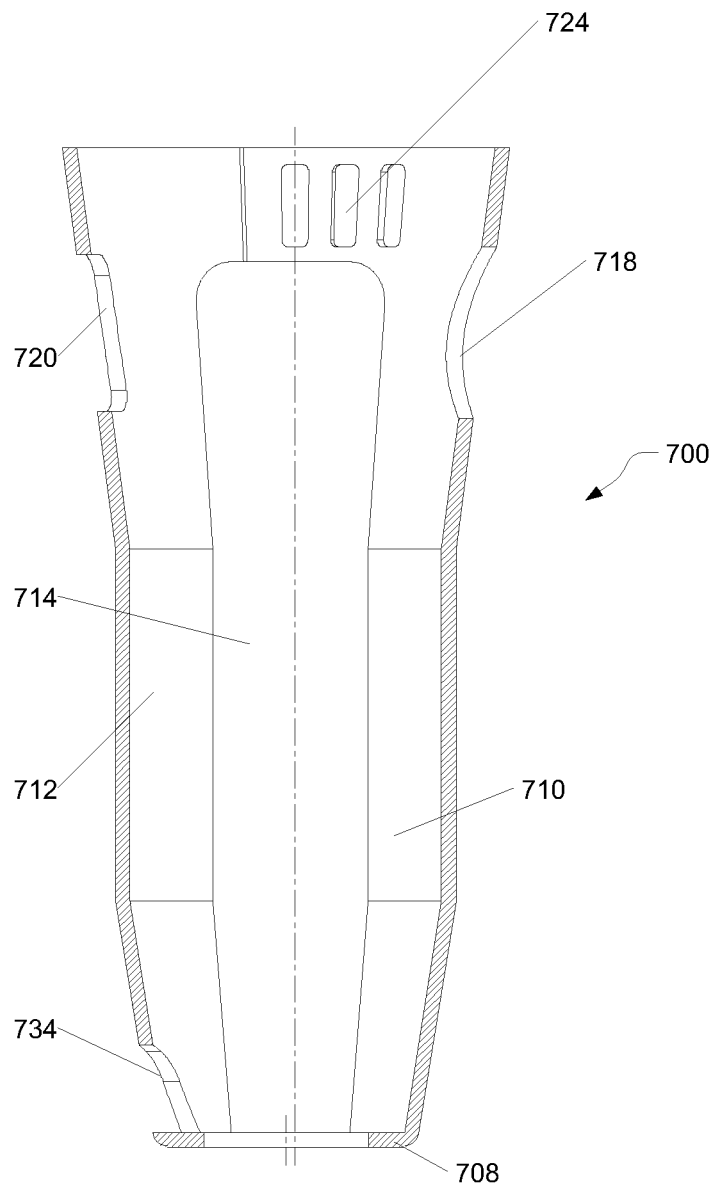
Figure 11:
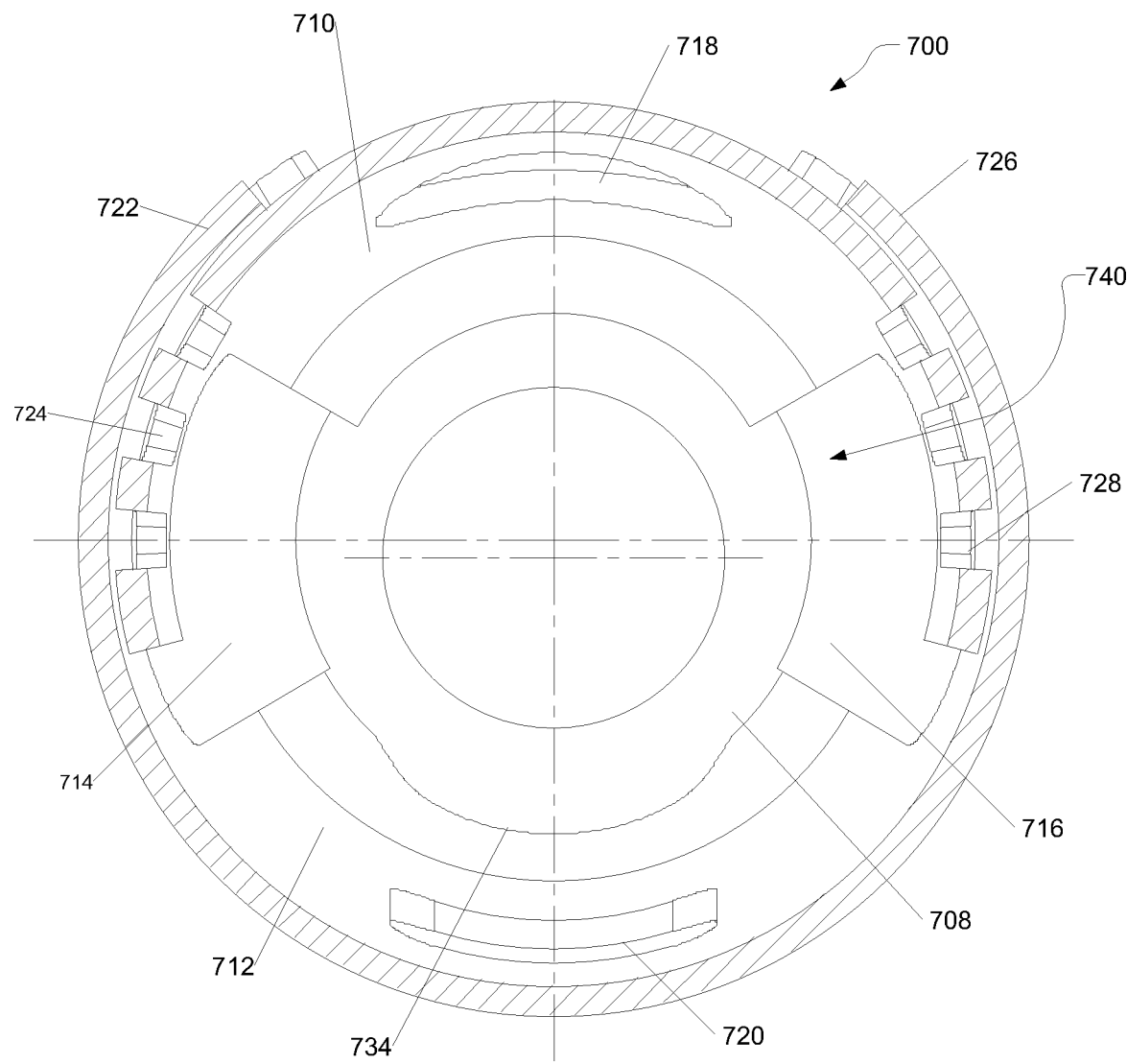
Figure 12:
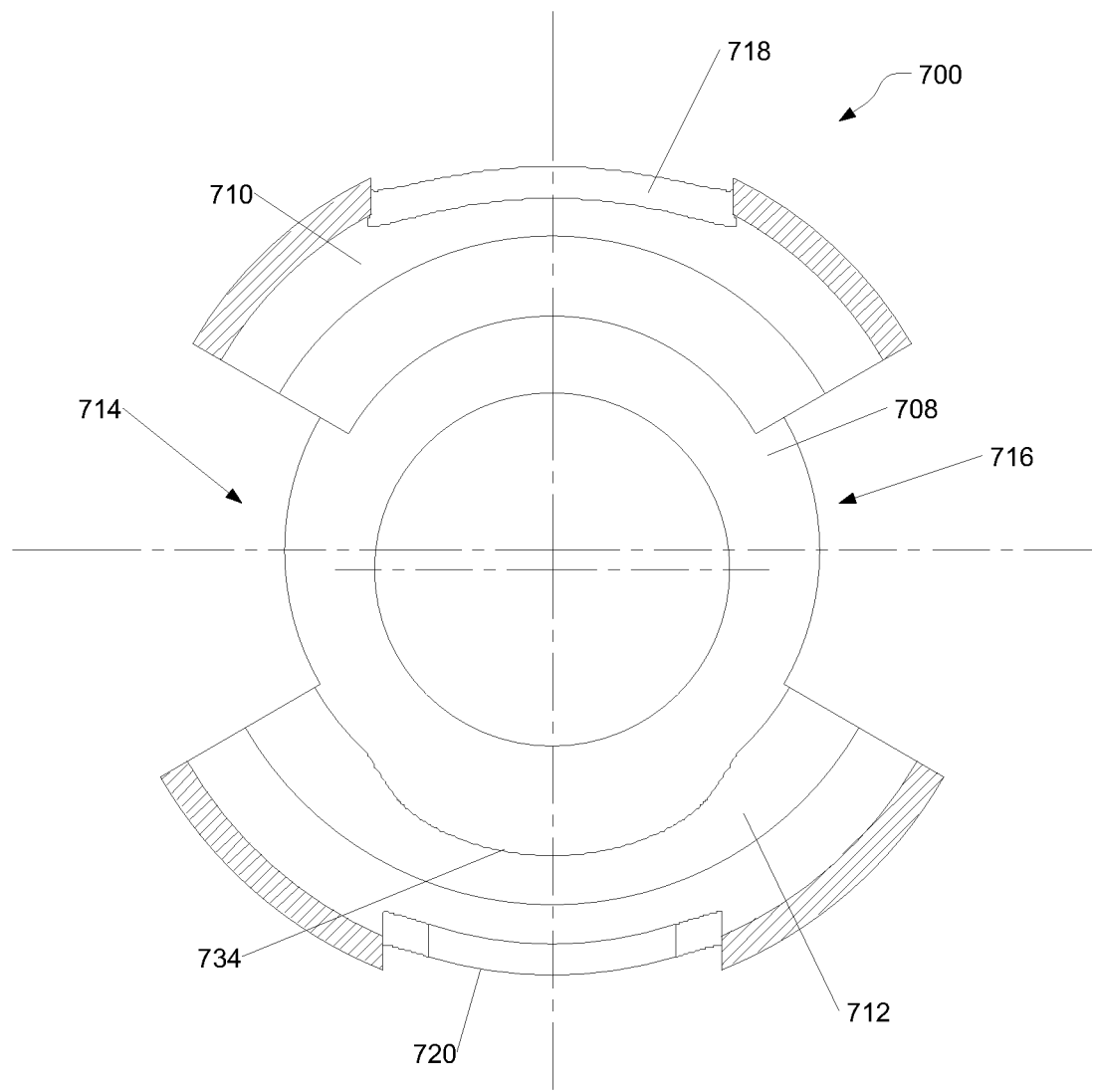

As illustrated in FIG. 11, the extender portions 710 and 712 may be arranged on opposite sides of the ring 708 relative to the major axis 706 (FIG. 8) and may define at least two side openings 714 and 716 between extender portions 710 and 712. As illustrated in FIG. 7 and FIG. 8, each of openings 714 and 716 may have a length parallel to the major axis 706 of the tissue extender 700 and a width perpendicular to the length. As further illustrated in FIG. 11, the extender portions 710 and 712 define a distal end opening, generally designated as 740 and disposed at the distal end 704 (FIG. 8) of the tissue extender 700.

In an example, a tool engagement feature 718, such as an opening, may be formed in the extender portion 710 and a tool engagement feature 720, such as an opening, may be formed in the extender portion 712. In particular, the tool engagement openings 718 and 720 are configured to engage a tool. For example, the tool may engage tool engagement features 718 and 720 of the tissue extender 700 to at least partially expand the tissue extender 700, such as by moving the distal ends of the extender portions 710 and 712 in opposite directions perpendicular to the major axis 706 of the tissue extender 700. In another example, the tool may act to detach the tissue extender 700 from the head of the subcutaneous screw, for example, by exerting force on the extender portions 710 and 172 along the major axis 706.

In particular, the tissue extender 700 may be expanded to retract soft tissue and provide access to the subcutaneous screw both percutaneously via the distal end 704 and subcutaneously via the side openings 714 and 716. Returning to FIG. 11, the tissue extender 700 includes coupling elements 722, 724, 726, and 728. For example, the extender portion 710 includes coupling elements 724 and 728, and the extender portion 712 includes coupling elements 722 and 726. When the tissue extender 700 is in an expanded position, the coupling element 722 may engage the coupling element 724, and the coupling element 726 may engage the coupling element 728 to maintain the tissue extender 700 in the expanded configuration. In the embodiment illustrated in FIGS. 7 through 12, the coupling elements 722 and 726 include tabs and the coupling elements 724 and 728 include sets of slots. In a particular example, the tabs (722 and 726) engages a slot of the set of slots (724 and 728) when the tissue extender 700 is in the expanded configuration. Alternatively, each extender portion 710 and 712 may include a tab on one side and a set of slots on an opposite side when viewed from the distal end 704, as illustrated in FIG. 11. In such an example, the tab of the extender portion 710 and a slot of the extender portion 712 may engage when the tissue extender is in an expanded position and a slot of the extender portion 710 and a tab of the extender portion 712 may engage when the tissue extender is in the expanded position. In further embodiments, coupling elements 722, 724, 726, and 728 may take other forms, such as dimples and holes or hooks and loops. In particular, expanding the tissue extender 700 may expand the distal end opening 740 and may at least partially expand the side openings 714 and 716 to provide improved access to the subcutaneous screw.

In a particular embodiment, the tissue extender 700 may be expanded to permit improved access to the subcutaneous screw. For example, the cross-sectional area of the distal end opening 740 may be increased by at least 1.5 times between the unexpanded and expanded configurations. In particular, the cross-sectional area of the distal end opening 740 may be increased at least 2.0 times, such as at least 2.5 times.

In addition, the width of the side openings 714 and 716 may be increase in the expanded configuration relative to the unexpanded configuration. For example, the width near the distal end of the side openings 714 and 716 may be increased at least 15%, such as at least 20%, or even at least 25%.

In an embodiment, the extender portions 710 and 712 are coupled to a ring 708 at a proximal end of the extender portions 710 and 712. As illustrated in FIG. 7 and FIG. 8, the ring 708 may include break features 730 and 732, such as notches or etched break lines. When the tissue expander 700 is removed from the head of the subcutaneous screw, a tool engages tool engagement elements 718 and 720 and causes the ring 708 to break at break features 730 and 732. As a result, the tissue expander 700 may be removed. Additionally, the extender portion 712 may include a proximal opening 734 adjacent to the ring 708.

Figure 13:
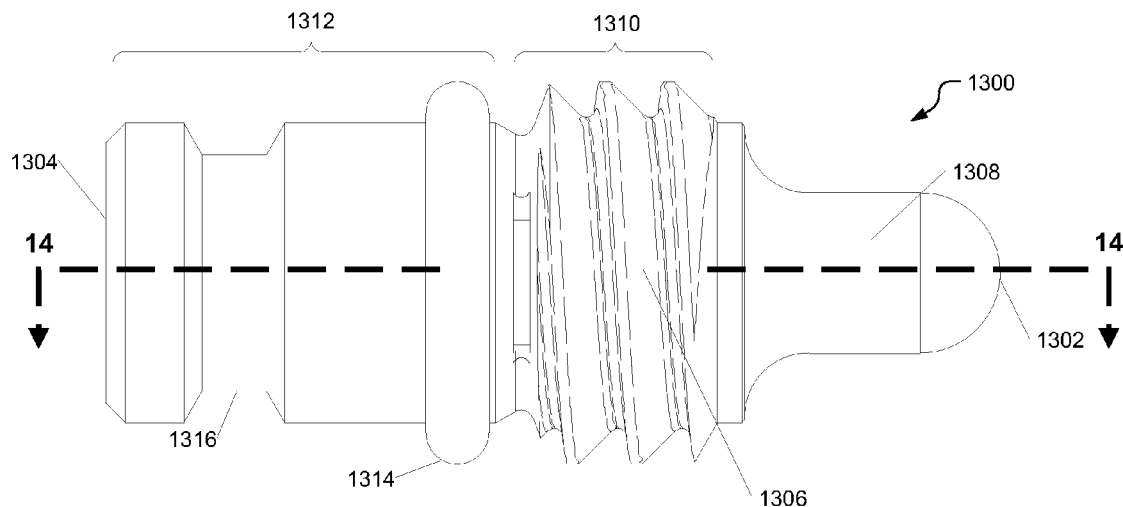
FIG. 13 and FIG. 14 include illustrations of exemplary setscrews.
Figure 14:
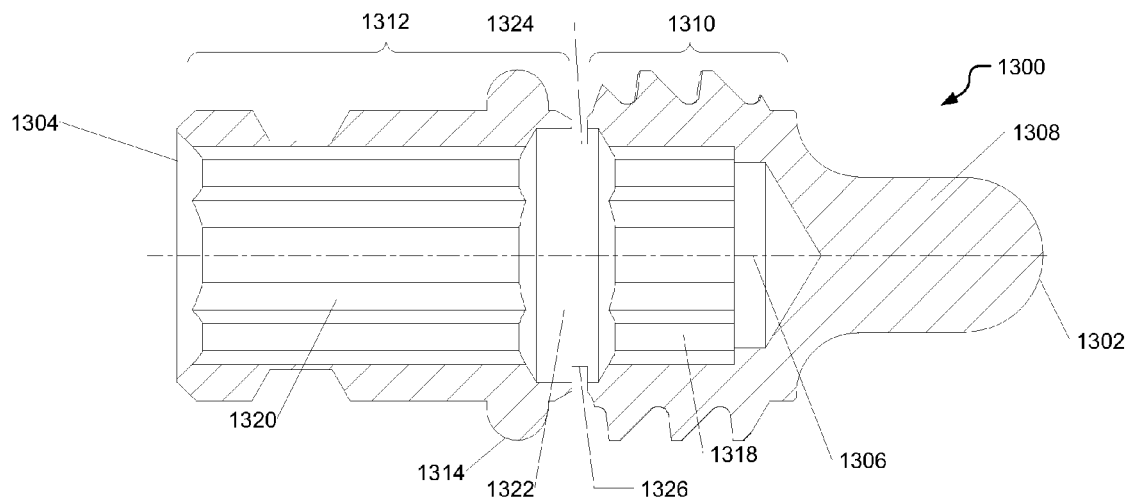

In addition to the subcutaneous screw and the percutaneous tissue extender, the percutaneous assembly may include a setscrew to secure elements to the subcutaneous screw. Referring to FIG. 13 and FIG. 14, a setscrew 1300 is illustrated. The setscrew 1300 may be used to secure an elongate element within a head of a subcutaneous screw, such as subcutaneous screw 400. As illustrate in FIG. 13, the setscrew 1300 has a proximal end 1302 and a distal end 1304 disposed along a major axis 1306. Starting from the proximal end 1302, the setscrew 1300 includes a proximal projection 1308, a threaded portion 1310, and a breakaway head 1312. The proximal projection 1308 may secure an elongate fixing element within the head of the subcutaneous screw. The threaded portion 1310 may engage an inner threaded region of the subcutaneous screw to hold the setscrew 1300 in place.

In an example, the breakaway head 1312 may be broken off the setscrew 1300, leaving the threaded portion 1310 engaged with the inner threaded region of the subcutaneous screw. The breakaway head 1312 includes a flange 1314 to prevent the setscrew 1300 from threading too deep into a head of a subcutaneous screw. Additionally, the breakaway head 1312 includes a channel 1316. For example, the channel 1316 may be used to retrieve the breakaway head 1312 from the head of the subcutaneous screw when the breakaway head 1312 has been detached from the setscrew 1300.

FIG. 14 illustrates a cross-section of the setscrew 1300 taken along line 14-14 of FIG. 13. Within the threaded portion 1310, the setscrew 1300 may have a lower tool engagement channel 1318. An upper tool engagement channel 1320 corresponding to the lower tool engagement channel 1318 may be formed within the breakaway head 1312. Between the breakaway head 1312 and the threaded portion 1310, a weakened region 1322 may be formed. Within the weakened region 1322, the wall of the setscrew 1300 may be thinner to allow easier breakage for removal of the breakaway head 1312. Additionally, a first cut 1324 and a second cut 1326 located between the breakaway head 1312 and the threaded portion 1310 may further weaken the setscrew 1300.

Figure 15:
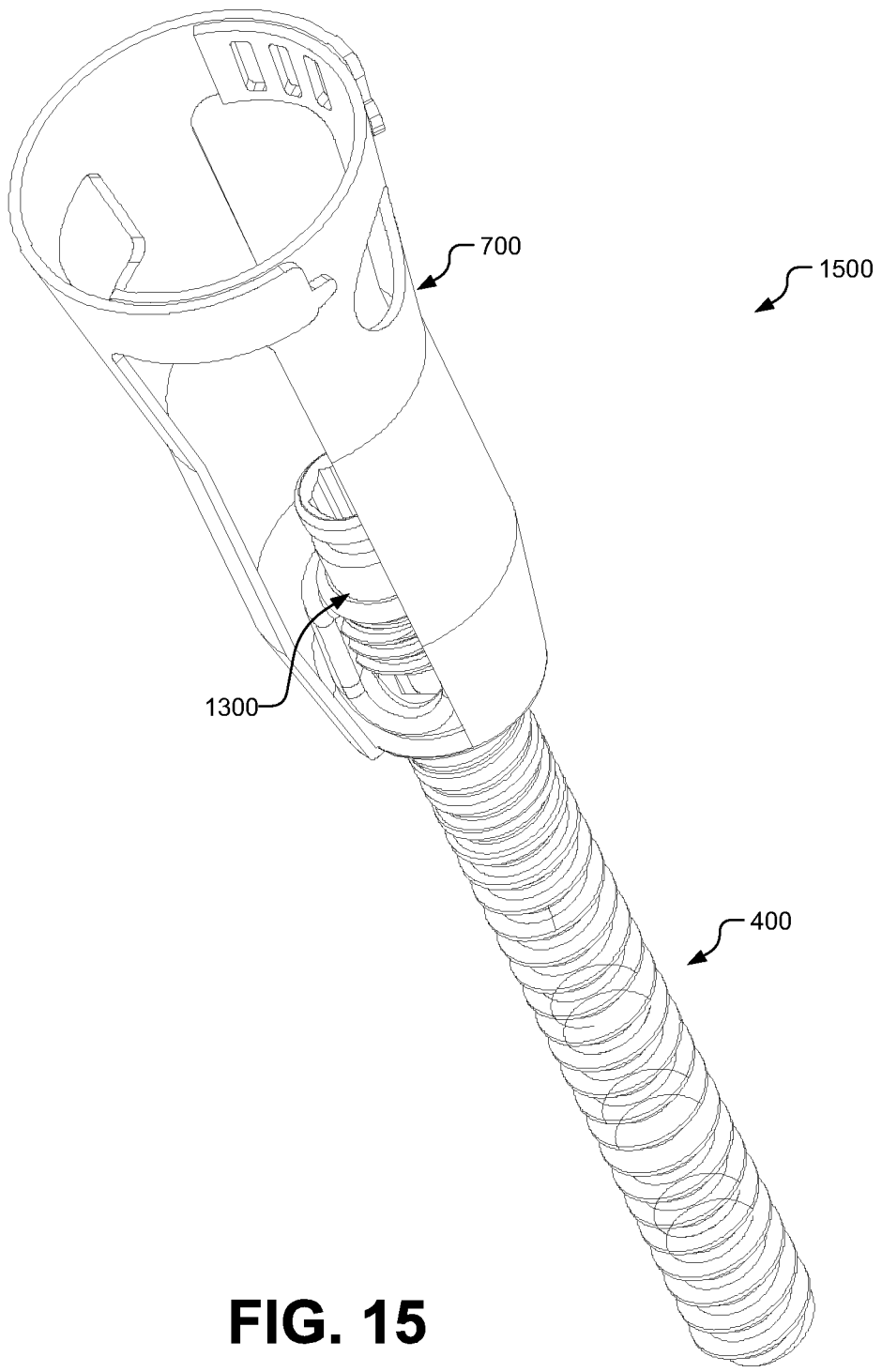
FIG. 15, FIG. 16, and FIG. 17 include illustrations of an exemplary assembly.
Figure 16:
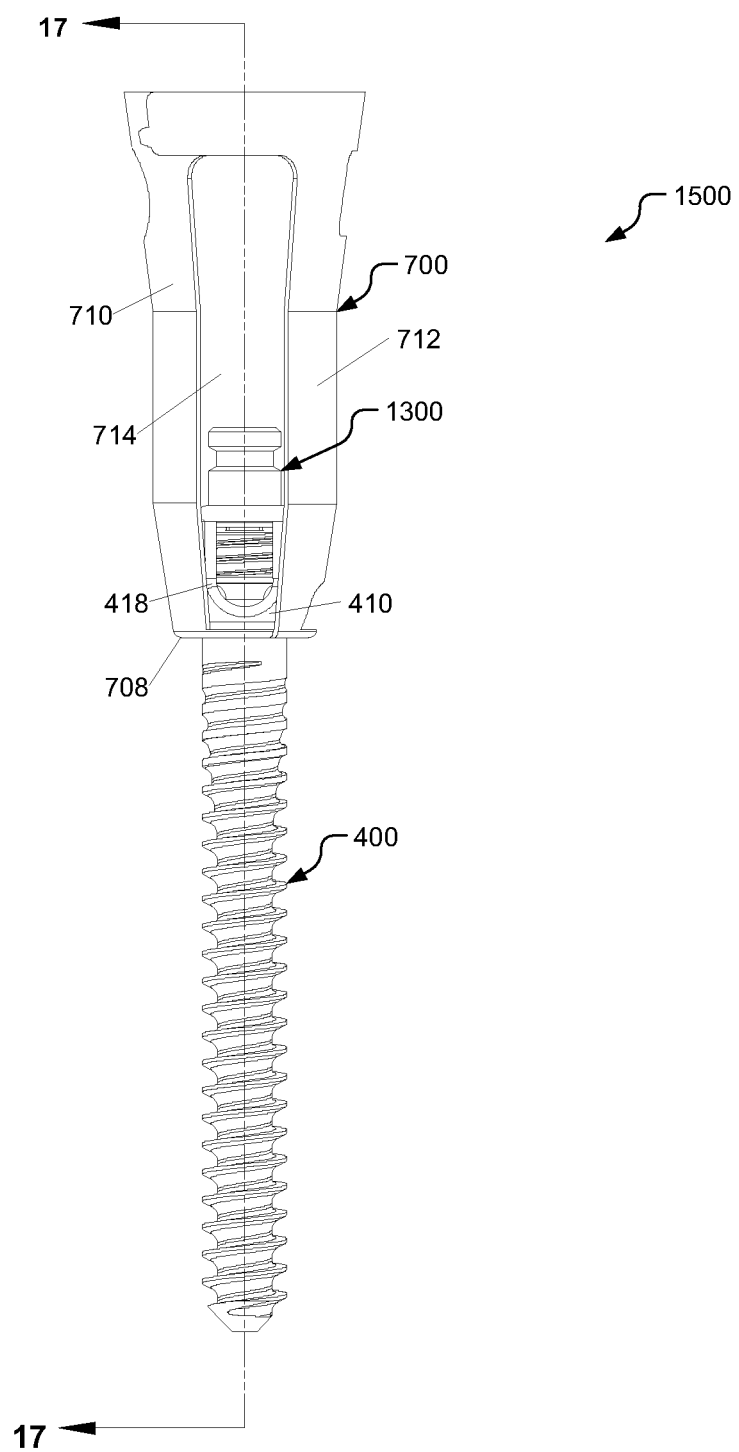
Figure 17:
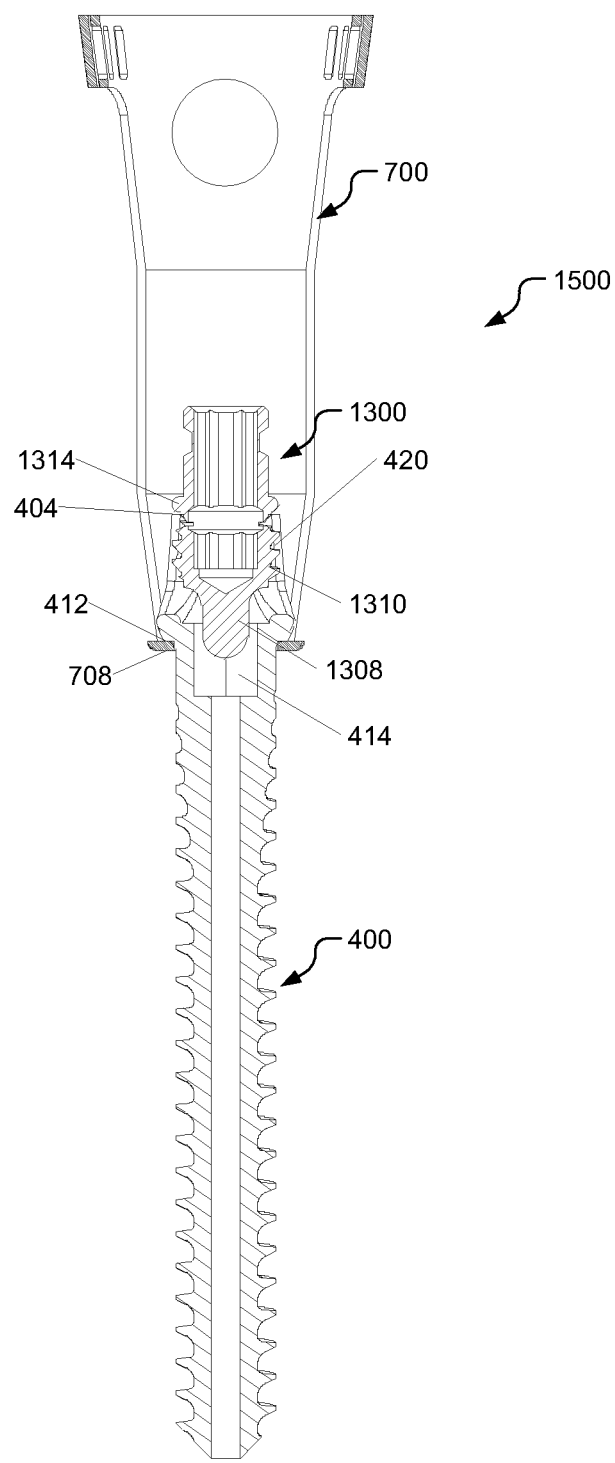

As illustrated in FIG. 15, FIG. 16, and FIG. 17, a percutaneous assembly 1500 includes the subcutaneous screw 400, the expandable tissue extender 700, and the setscrew 1300. As illustrated in FIG. 16, the width of the openings 714 between the extender portions 710, 712 may be less than the width of the head 410 of the subcutaneous screw 400 and greater than the width of the slot 418 in the head 410.

In an embodiment illustrated in FIG. 17, the ring 708 of the tissue expander 700 engages the lip 412 of the subcutaneous screw 400. Additionally, the threaded portion 1310 of the setscrew 1300 engages the inner threaded portion 420 of the head 410 of the subcutaneous screw 400. The proximal projection 1308 of the setscrew 1300 may extend into the tool engagement depression 414 of the subcutaneous screw 400 to secure an elongated fixing element, such as a wire, a rod, or a tether. The flange 1314 of the setscrew 1300 contacts the proximal end 404 of the head 410 of the subcutaneous screw 400, preventing the setscrew 1300 from advancing further into the subcutaneous screw 400.

Figure 24:
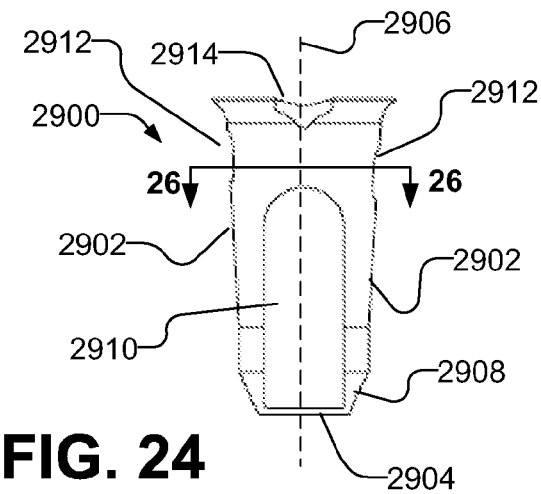
FIG. 24, FIG. 25, and FIG. 26 include illustrations of exemplary tissue extenders.
Figure 25:
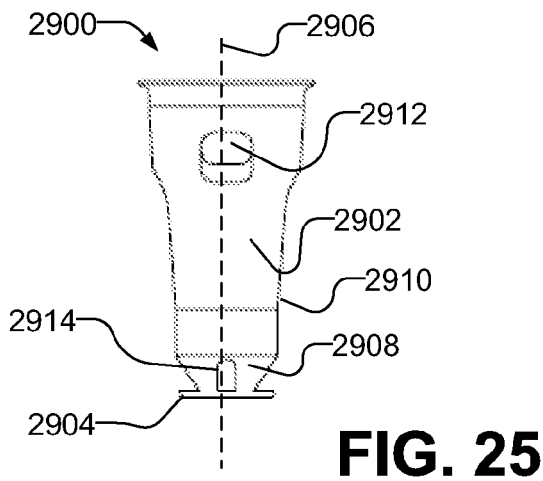
Figure 26:
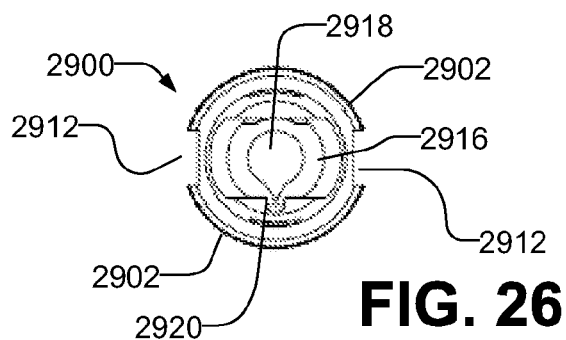

In an alternative embodiment, the tissue extender may be formed of a single piece or may not be expandable. As illustrated in FIG. 24, FIG. 25, and FIG. 26, a tissue extender 2900 may define two side walls, such as a first wall and a second wall 2902 attached at a proximal end to a ring 2904. The side walls 2902 at the proximal end define a shoulder 2908 having increasing radius moving away from the ring 2904 and proximal end toward the distal end of the tissue extender 2900. The two side walls 2902 join at a distal end to form a distal end opening and a cavity as illustrated in FIG. 26.

In an example, the two side walls 2902 define two elongated axial windows 2910 that provide access to a head of a subcutaneous screw. In addition, each side wall 2902 defines a tool engagement structure 2912, such as an opening that may be engaged by a removal tool. In another example, a notch 2914 may be located at the distal end of the tissue extender 2900 and may align with the opening 2910.

In a further example, each side wall 2902 defines an opening 2914, which may be engaged to prevent rotation when a subcutaneous screw is being implanted into an osteal structure. Such openings 2914 may also add to weaken the ring 2904 to aid in removal of the tissue extender 2900.

Figure 27:
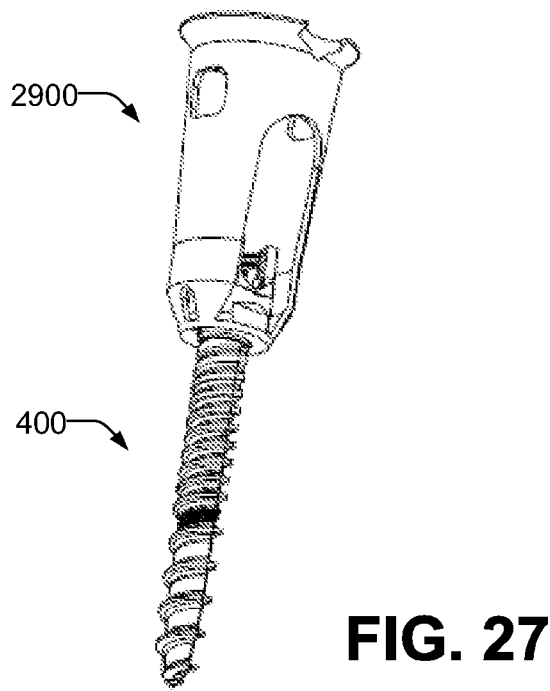
FIG. 27 includes an illustration of an exemplary assembly.

In a particular example, the side walls 2902 define a central cavity 2916 and a distal end opening when viewed in cross-section perpendicular to the axis 2906, as illustrated in FIG. 26. In addition, the ring 2904 may define an opening 2918 through which a subcutaneous screw, such as a pedicle screw may extend. Accordingly, the ring 2904 may engage a head of the pedicle screw 400 as illustrated in FIG. 27. In addition, a notch 2920 may be provided in the ring 2904, weakening the ring 2904 to assist with removing the tissue extender 2900.

Description of Tool for Use in Conjunction with the Percutaneous Assembly

Figure 18:
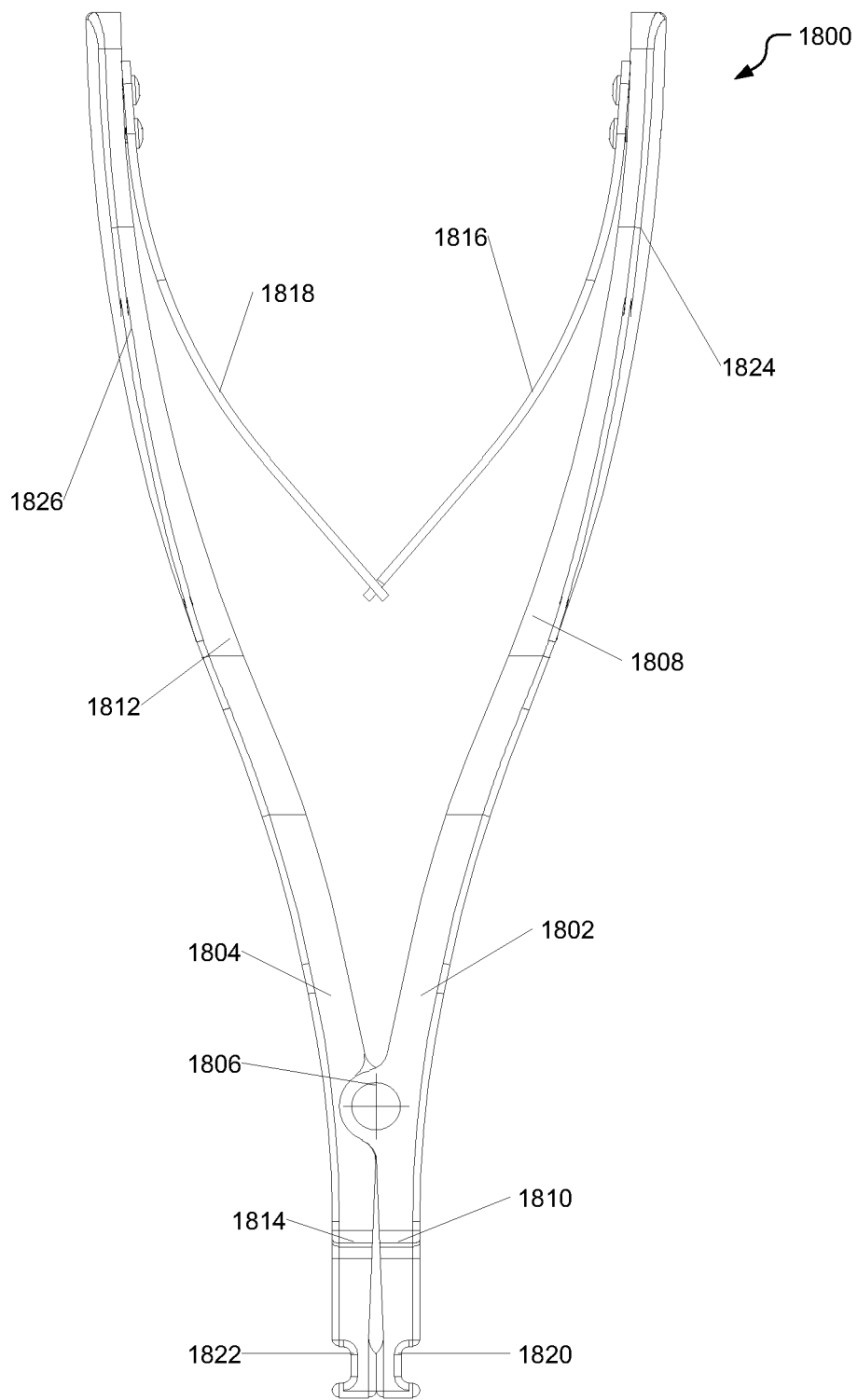
FIG. 18, FIG. 19, FIG. 20, and FIG. 21 include illustrations of exemplary tools for use in conjunction with the exemplary assembly.

FIG. 18 illustrates an expansion tool 1800 for expanding a tissue extender, such as tissue extender 700. The expansion tool 1800 may include an arm 1802 and an arm 1804 pivotally connected at a pivot point 1806. The arm 1802 may include a handle 1808 at a first end 1824 and may include a second end 1810, and the arm 1804 may include a handle 1812 at a first end 1826 and may include a second end 1814. As illustrated, the second end 1810 of the first arm 1802 and the second end 1814 of the arm 1804 travel in opposite directions when the handles 1808 and 1812 are moved toward one another.

A spring bar 1816 may be attached to the handle 1808 and may engage a spring bar 1818 attached to the handle 1812. The spring bars 1816 and 1818 motivate the handles 1808 and 1812 apart, bringing ends 1810 and 1812 closer together.

In a particular example, the end 1810 may include a tissue extender engagement element 1820 and the end 1814 may include a tissue extender engagement element 1822. As illustrated, the tissue extender engagement elements 1820 and 1822 are concave features to engage features of a tissue extender. In particular, the tissue extender engagement elements 1820 and 1822 may engage tool engagement openings 718 and 720 of the tissue extender 700. When the handles 1808 and 1812 are forced together, the ends 1810 and 1814 are forced apart and the tissue extender engagement elements 1820 and 1822 may force the extender portions 710 and 712 apart, moving the tissue extender 700 into an expanded configuration.

Figure 19:
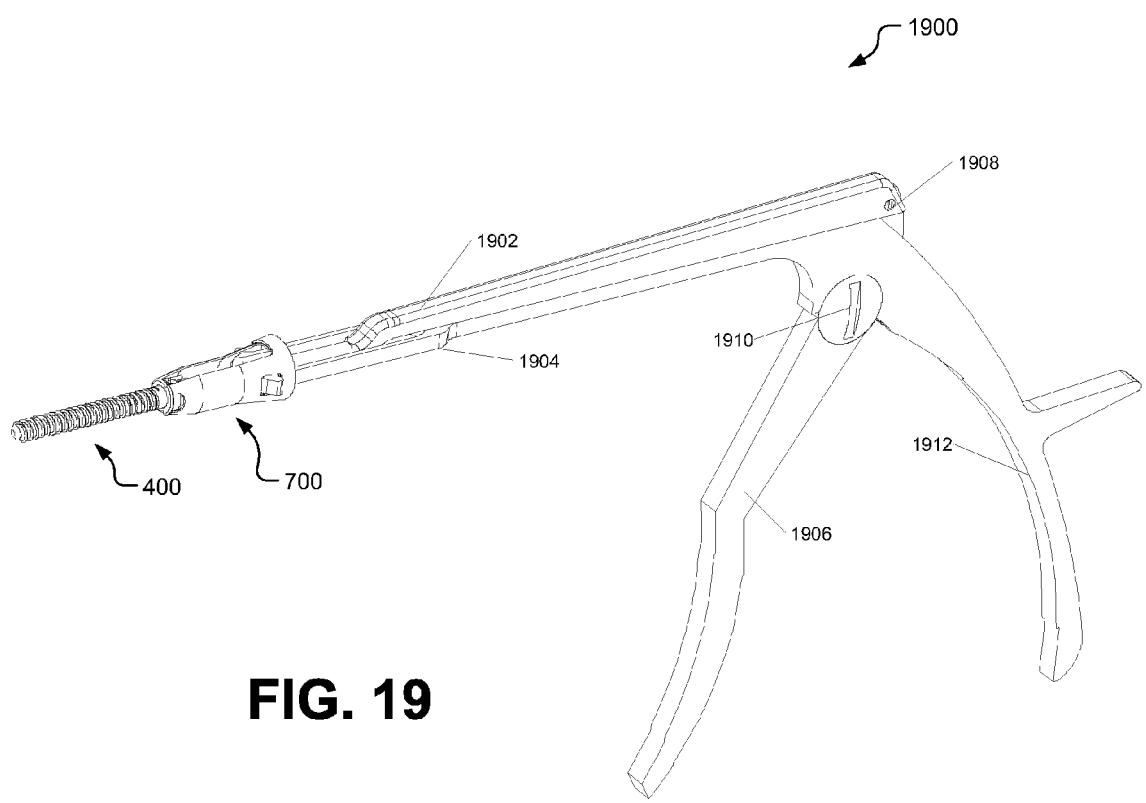
Figure 20:
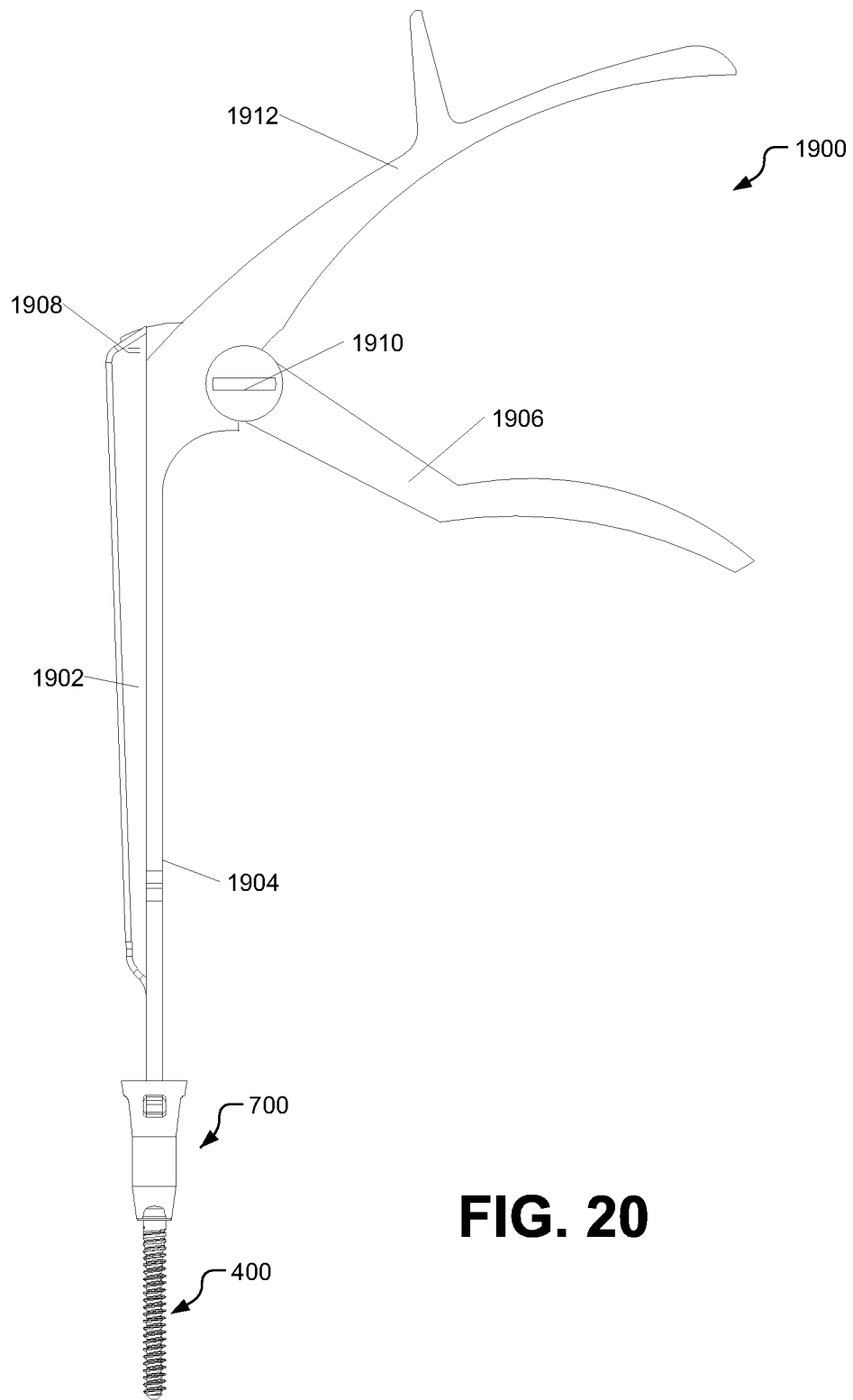
Figure 21:
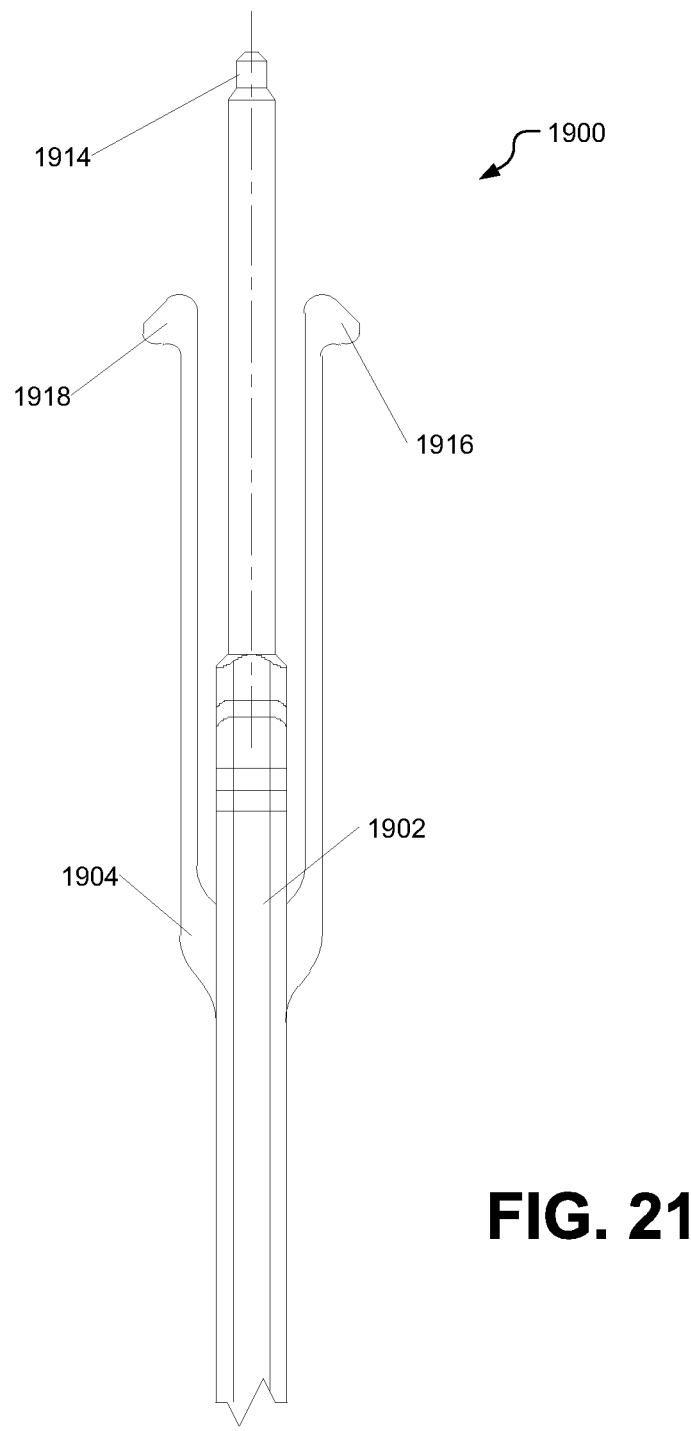

In another embodiment, a tool may engage the tissue extender to detach the tissue extender from the subcutaneous screw for removal of the tissue extender. Referring to FIG. 19, FIG. 20, and FIG. 21, a removal tool 1900 may be configured to engage a tissue extender 700 and a subcutaneous screw 400. As illustrated in FIG. 19, the removal tool 1900 includes an arm 1902, an arm 1904, and a handle 1906. The arm 1904 also defines a handle 1912. In an example, the arm 1902 is pivotally attached to the handle 1906 at an attachment point 1908. Additionally, the arm 1904 is pivotally attached to the handle 1906 at a pivot point 1910. When the handle 1906 is motivated toward the handle 1912, the arm 1902 is biased forward relative to an end of the arm 1904.

As illustrated in FIG. 21, the arm 1902 includes a screw contacting element 1914, and an end of the arm 1904 opposite the handle 1912 includes tissue expander engagement elements 1916 and 1918. When the screw contacting element 1914 engages the subcutaneous screw 400 and the tissue expander engagement elements 1916 and 1918 engage the tissue extender 700, as illustrated in FIG. 19 and FIG. 20, movement of the handle 1906 towards the handle portion 1912 forces the subcutaneous screw 400 and the tissue extender 700 in opposite directions. In particular, such force may break a ring of the tissue extender 700 and may detach the tissue extender 700 from the subcutaneous screw 400. During a surgical procedure, the tissue extender 700 may be removed percutaneously and the surgical site closed.

Description of Methods of Treating a Spine

Figure 22:
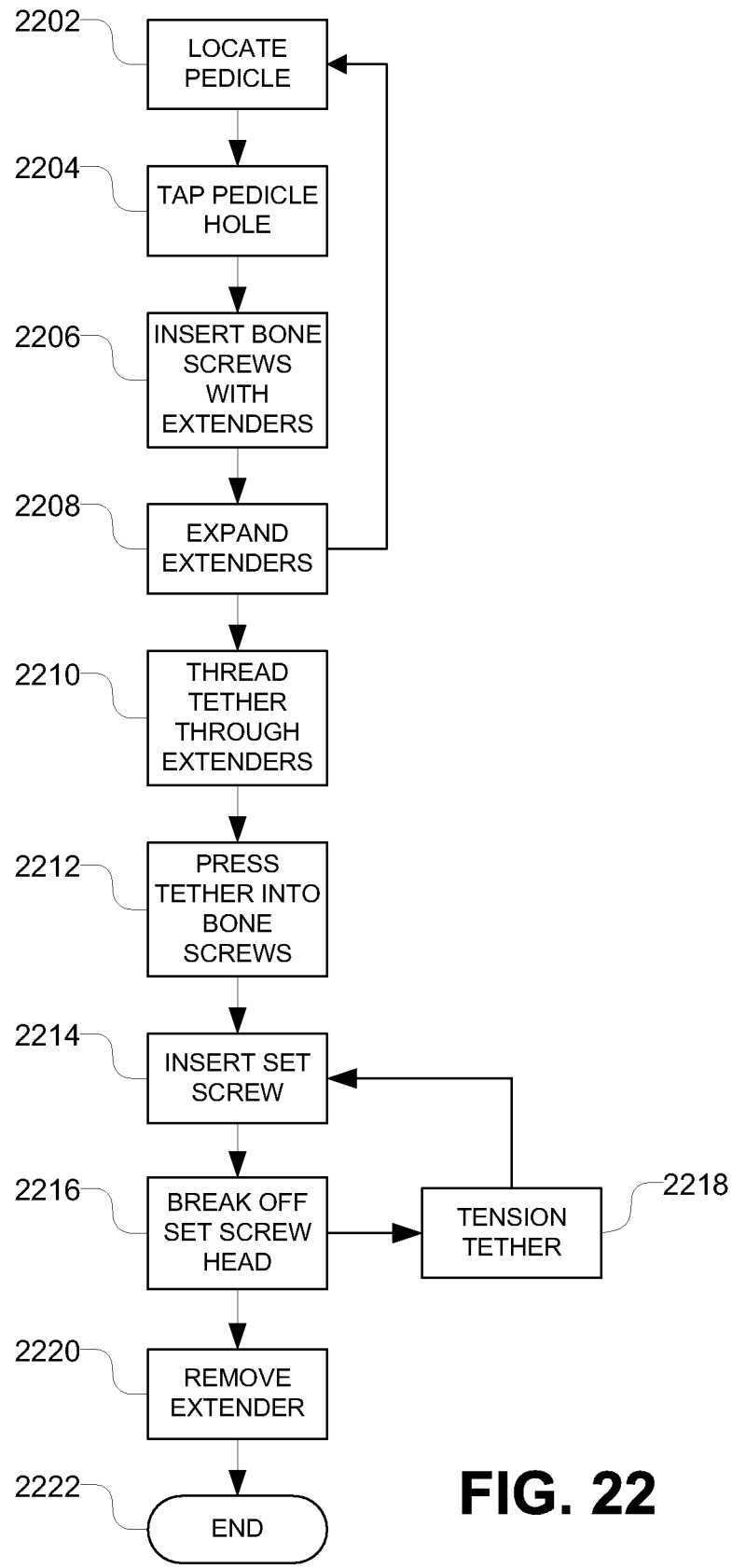
FIG. 22 includes a flow diagram illustrating an exemplary surgical method.

Referring to FIG. 22, a method of treating a spine is illustrated. As illustrated at 2202, a pedicle may be located. For example, a probe may be used to locate the pedicle. Generally, radiological imaging, such as x-ray imaging, computed tomography x-ray imaging, or magnetic resonance imaging, is performed prior to initiating a surgery to determine the relative position of vertebrae. When the surgeon has located the vertebra of choice, a small incision is made in the skin overlying the vertebra and access to the vertebra is formed.

As illustrated at 2204, a hole or indentation may be formed in the pedicle of the vertebra. For example, a tap may be used to form the indentation. In a particular example, a guidewire may be secured to the indentation to guide a subcutaneous screw. Alternatively, the procedure may be performed absent the guidewire.

As illustrated at 2206, a subcutaneous screw with a tissue extender may be inserted through the incision and the subcutaneous screw may be driven into the tunnel, or passage, created within the pedicle. The subcutaneous screw may have a threaded shaft and a head coupled to the threaded shaft. In addition, the head of the subcutaneous screw may have a channel to receive an elongated fixing element. The position of the head relative to the threaded shaft may be fixed, or the head may be able to move relative to the threaded shaft, such as by rotating around one or more axis. For example, the head of a polyaxial subcutaneous screw may have more than one axis of rotation.

When the subcutaneous screw is inserted and driven in to the pedicle of the vertebra, the attached tissue extender extends from the head of the subcutaneous screw through the soft tissues adjacent the pedicle and through the skin, providing access to the head of the subcutaneous screw percutaneously. As illustrated at 2208, the extender may be expanded. For example, an expansion tool may be used to expand the percutaneous tissue extender. In general, expansion of the tissue extender may increase the size of an opening in the extender, such as a distal end opening or a side opening. In a particular example, coupling elements of the extender portions of the tissue extender may engage to maintain the extender in an expanded position. Additionally, expansion of the tissue extender may increase the field of view of the head of the subcutaneous screw, such as by forcing tissue out of the way and enlarging the distal end opening.

In a particular embodiment, steps illustrated at 2202 through 2208 may be repeated to insert multiple subcutaneous screws and thus, multiple percutaneous surgical assemblies. In an example, multiple subcutaneous screws may be inserted in a set of vertebrae. In another example, multiple subcutaneous screws may be inserted in to a single vertebra, for example, one into each pedicle of the vertebra.

As illustrated at 2210, an elongated fixing element may be inserted through side openings of the tissue extender. In an example, the elongated fixing element may include a wire, a tether, or a rod. In particular the elongated fixing element may at least partially limit the relative movement of two vertebrae. For example, the elongated fixing element may be a tether, and a needle may be attached to a tether to guide the tether through tissue surrounding the subcutaneous screw and the tissue extender and through the side openings of the tissue extender.

As illustrated at 2212, the tether may be pressed into a channel within the head of the subcutaneous screw. For example, as illustrated at 2214, a setscrew is inserted into the head of the subcutaneous screw to hold the tether within the head of the subcutaneous screw. In an example, the setscrew secures the tether to prevent sliding of the tether. Alternatively, the setscrew may secure the position of the tether, but may allow the tether to slide through the head of the subcutaneous screw. As illustrated at 2216, a breakaway head of the setscrew may be removed upon securing the tether with the setscrew.

When multiple percutaneous screw systems are in place, an elongated fixing device, such as a rod, a wire, or a tether, may be inserted through the side openings of each of the tissue extenders. For example, a needle attached to a tether may be manipulated through soft tissue proximate to each of the vertebra and through each of the tissue extenders. The tether may be drawn through each of the issue extenders and positioned within the channel of the subcutaneous screw. In a particular example, the tether is fixedly secured to a first of the subcutaneous screws, tension is applied, and the tether is fixedly secured to a second of the subcutaneous screws. For example, as illustrated at 2218, the tether may be tensioned. In particular, the tether may be tensioned to limit the relative motion between the vertebrae. For example, the tether may be tensioned before securing the tether between each set of adjacent vertebrae. In another example, the tether may be tensioned once and the setscrew applied. In a further exemplary embodiment, the tether may be partially secured and allowed to slide through a subset of the subcutaneous screws. In particular, a setscrew may be applied, the breakaway end may be removed and tension may be applied to the tether, followed by applying a second setscrew, removing the breakaway end, and further tensioning of the tether.

As illustrated at 2220, the tissue extender may be removed. For example, a tissue extender removal tool may break the ring of the tissue extender so that the tissue extender may be removed from the head of the subcutaneous screw and out of the patient percutaneously. The method may end, as illustrated at 2222. For example, the soft tissue adjacent the vertebrae may move back into position and the soft tissues including the skin may be sutured to close the surgical site.

Description of a Surgical Kit

Figure 23:
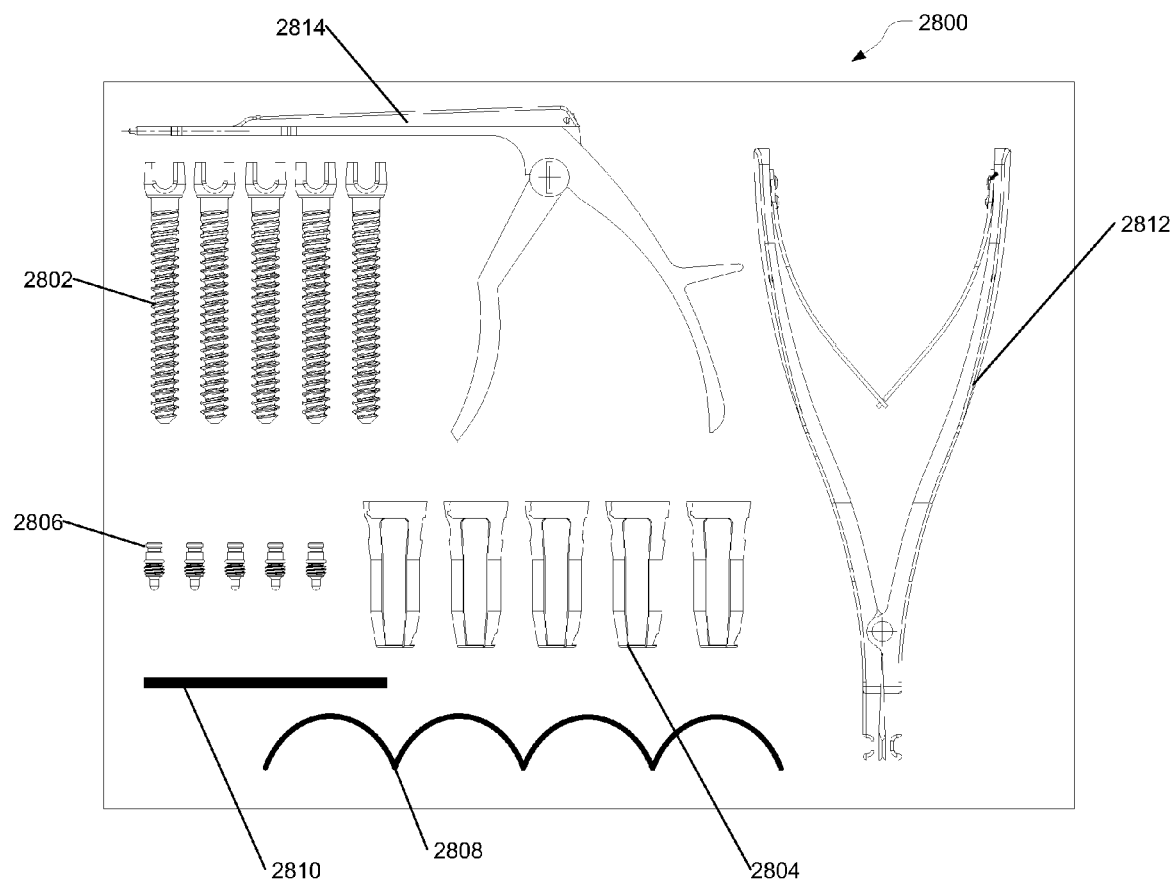
FIG. 23 includes an illustration of an exemplary surgical kit.

In a particular embodiment, elements of the percutaneous surgical assembly may be included in a surgical kit. Referring to FIG. 23, a kit 2800 is shown. The kit 2800 may include a plurality of subcutaneous screws 2802, a plurality of tissue extenders 2804, and a plurality of setscrews 2806. The subcutaneous screws may be similar to subcutaneous screw 400, the tissue extenders 2804 may be similar to tissue extender 700, and the setscrews 2806 may be similar to setscrew 1300. Additionally, the kit 2800 may include a tether 2808 and a needle 2810. Further, the kit 2800 may include an expansion tool 2812 and a removal tool 2814. The expansion tool 2812 may be similar to expansion tool 1800, and removal tool 2814 may be similar to removal tool 1900. In addition, the kit 2800 may include a tensioning tool.

In general, one or more of the above elements may be stored in a sterilized package together. For example, the plurality of subcutaneous screws 2802, the plurality of tissue extenders 2804, and the plurality of setscrews 2806 may be housed within a sterilized package.

CONCLUSION

With the configuration of structure described above, fixing an elongated fixing element, such as a tether, to subcutaneous screws inserted into the vertebrae provides a method that may be used to treat a spine and substantially alleviate or minimize one or more symptoms associated with disc degeneration, facet joint degeneration, vertebral misalignment, or a combination thereof. For example, the tether may be installed between pedicles of adjacent vertebrae to maintain them at or near a predetermined distance there between.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes may be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A tissue extender, comprising:
   a ring defining a proximal end opening to engage a head of an implantable subcutaneous screw and including a break feature configured to fracture the ring upon force application such that the tissue extender is removable from the head without extracting the subcutaneous screw;
   a first extender portion coupled to the ring at a proximal end of the first extender portion, the first extender portion including a first coupling portion disposed at a distal end of the first extender portion; and
   a second extender portion coupled to the ring at a proximal end of the second extender portion, the second extender portion including a second coupling portion at a distal end of the second extender portion;
   wherein the tissue extender is configured to extend from the head of the implantable subcutaneous screw through tissue adjacent the subcutaneous screw and outside a periphery of the tissue when the subcutaneous screw is in a fully implanted configuration;
   wherein the first and second extender portions define two side openings disposed on opposite sides of the tissue extender;

wherein the distal ends of the first and second extender portions together define a distal end opening; and wherein the first coupling portion engages the second coupling portion when the tissue extender is in an extended state, the distal end opening being larger in the extended state than in an unextended state.

2. The tissue extender of claim 1, wherein the two side openings extend parallel to a major axis of the tissue extender.

3. The tissue extender of claim 1, wherein the two side openings have a width greater than the width of a slot in a head of the subcutaneous screw.

4. The tissue extender of claim 1, wherein the two side openings have a width less than the width of a head of the subcutaneous screw.

5. The tissue extender of claim 1, wherein the subcutaneous screw is a pedicle screw.

6. The tissue extender of claim 1, wherein the first coupling portion includes a tab and the second coupling portion includes a slot, the tab to engage the slot when the tissue extended is in an extended state.

7. The tissue extender of claim 1, wherein the first extender portion includes a third coupling portion and the second extender portion includes a forth coupling portion, the third coupling portion to engage the forth coupling portion when the tissue extender is in an extended state.

8. The tissue extender of claim 1, wherein the first and second extender portions each include a tool engagement feature.

9. The tissue extender of claim 8, wherein an expander tool is to engage the tool engagement feature of each of the first and second extender portions to expand the tissue extender to the expanded state.

10. The tissue extender of claim 8, wherein a removal tool is to engage the tool engagement features of each of the first and second extender portions to detach the tissue extender from the subcutaneous screw.

11. The tissue extender of claim 1, wherein the second extender portion includes a proximal extender opening.

12. The tissue extender of claim 1, wherein the break feature is selected from the group consisting of notches and etched break lines.

13. A percutaneous surgical assembly, comprising:
an implantable subcutaneous screw having a threaded shaft and a head; and
a tissue extender, including:
a ring defining a proximal end opening to engage the head of the subcutaneous screw and including a break feature configured to fracture the ring upon force application such that the tissue extender is removable from the head without extracting the subcutaneous screw;
a first extender portion coupled to the ring at a proximal end of the first extender portion, the first extender portion including a first coupling portion disposed at a distal end of the first extender portion; and
a second extender portion coupled to the ring at a proximal end of the second extender portion, the second extender portion including a second coupling portion at a distal end of the second extender portion;
wherein the tissue extender is configured to extend from the head of the implantable subcutaneous screw through tissue adjacent the subcutaneous screw and outside a periphery of the tissue when the subcutaneous screw is in a fully implanted configuration;
wherein the first and second extender portions define two side openings disposed on opposite sides of the tissue extender;
wherein the distal ends of the first and second extender portions together define a distal end opening; and
wherein the first coupling portion engages the second coupling portion when the tissue extender is in an extended state, the distal end opening being larger in the extended state than in an unextended state.

14. The percutaneous surgical assembly of claim 13, wherein the two side openings extend parallel to a major axis of the tissue extender.

15. The percutaneous surgical assembly of claim 13, wherein the head of the subcutaneous screw includes a slot and the two side openings have a width greater than the width of the slot.

16. The percutaneous surgical assembly of claim 13, wherein the two side openings have a width less than the diameter of the head of the subcutaneous screw.

17. The percutaneous surgical assembly of claim 13, wherein the subcutaneous screw is a pedicle screw to engage the pedicle of a vertebra.

18. The percutaneous surgical assembly of claim 13, wherein the first coupling portion includes a tab and the second coupling portion includes a slot, the tab to engage the slot when the tissue extender is in an extended state.

19. The percutaneous surgical assembly of claim 13, wherein the first extender portion includes a third coupling portion and the second extender portion includes a forth coupling portion, the third coupling portion engages the forth coupling portion when the tissue extender is in an extended state.

20. A method of performing osteal surgery, the method comprising:
driving a percutaneous surgical assembly into a pedicle of a vertebra, the percutaneous surgical assembly including an implanted subcutaneous screw and a tissue extender, the tissue extender including:
a ring defining a proximal end opening to engage a head of the subcutaneous screw and including a break feature configured to fracture the ring upon force application such that the tissue extender is removable from the head without extracting the subcutaneous screw;
a first extender portion coupled to the ring at a proximal end of the first extender portion, the first extender portion including a first coupling portion disposed at a distal end of the first extender portion; and
a second extender portion coupled to the ring at a proximal end of the second extender portion, the second extender portion including a second coupling portion at a distal end of the second extender portion;
wherein the tissue extender is configured to extend from the head of the implantable subcutaneous screw through tissue adjacent the subcutaneous screw and outside a periphery of the tissue when the subcutaneous screw is in a fully implanted configuration;
wherein the first and second extender portions define two side openings disposed on opposite sides of the tissue extender; and
wherein the distal ends of the first and second extender portions together define a distal end opening; and
expanding the tissue extender to an extended state, the first coupling portion engaging the second coupling portion, the distal end opening being larger in the extended state than in an unextended state.

21. The method of claim 20, further comprising threading a tether through the first and second side openings.

22. The method of claim 21, further comprising securing the tether to the head of the subcutaneous screw.

23. The method of claim 20, further comprising removing the tissue extender.

24. A surgical kit, comprising:
a plurality of implantable pedicle screws;
a plurality of tissue extenders, each tissue extender of the plurality of tissue extenders comprising:
   a ring defining a proximal end opening to engage a head of a pedicle screw and including a break feature configured to fracture the ring upon force application such that each tissue extender is removable from the head without extracting the pedicle screw;
   a first extender portion coupled to the ring at a proximal end of the first extender portion, the first extender portion including a first coupling portion disposed at a distal end of the first extender portion; and
   a second extender portion coupled to the ring at a proximal end of the second extender portion, the second extender portion including a second coupling portion at a distal end of the second extender portion;
wherein the tissue extender is configured to extend from the head of the implantable subcutaneous screw through tissue adjacent the pedicle screw and outside a periphery of the tissue when the subcutaneous screw is in a fully implanted configuration;
wherein the first and second extender portions define two side openings disposed on opposite sides of the tissue extender;
wherein the distal ends of the first and second extender portions together define a distal end opening; and
wherein the first coupling portion engages the second coupling portion when the tissue extender is in an extended state, the distal end opening being larger in the extended state than in an unextended state; and an elongated fixing device.

25. A tissue extender, comprising:
a ring defining a proximal end opening to engage a head of an implantable subcutaneous screw and including a break feature configured to fracture the ring upon force application such that the tissue extender is removable from the head without extracting the subcutaneous screw;
a first side wall coupled to the ring at a proximal end of the first side wall, the first side wall defining a first tool engagement opening; and
a second side wall coupled to the ring at a proximal end of the second side wall, the second side wall defining a second tool engagement opening;
wherein the tissue extender is configured to extend from the head of the implantable subcutaneous screw through tissue adjacent the subcutaneous screw and outside a periphery of the tissue when the subcutaneous screw is in a fully implanted configuration;
wherein the first and second side walls join at a distal end to define a distal end opening; and
wherein the first and second side walls define two side openings disposed on opposite sides of the tissue extender to provide access to the head of the subcutaneous screw.

26. A tissue extender, comprising:
a ring defining a proximal end opening to engage a head of an implantable subcutaneous screw and including a break feature configured to fracture the ring upon force application such that the tissue extender is removable from the head without extracting the subcutaneous screw;
a first extender portion coupled to the ring at a proximal end of the first extender portion the first extender including a first coupling element; and
a second extender portion coupled to the ring at a proximal end of the second extender portion, the second extender including a second element configured to engage the first coupling element;
wherein the tissue extender is configured to extend from the head of the implantable subcutaneous screw through tissue adjacent the subcutaneous screw and outside a periphery of the tissue when the subcutaneous screw is in a fully implanted configuration;
wherein distal ends of the first and second extender portions are movable toward each other in an unextended state and movable away from each other in an extended state such that the first and second coupling elements are engaged to maintain the extended state; and
a space between the distal ends is larger in the extended state than in an unextended state.

* * * * *